US00RE39920E

(19) United States
(12) Reissued Patent
Umansky et al.

(10) Patent Number: US RE39,920 E
(45) **Date of Reissued Patent: *Nov. 13, 2007**

(54) METHODS FOR DETECTION OF NUCLEIC ACID SEQUENCES IN URINE

(75) Inventors: Samuil R. Umansky, Princeton, NJ (US); Anatoly V. Lichtenstein, Moscow (RU); Hovsep S. Melkonyan, Princeton, NJ (US)

(73) Assignee: Xenomics, Inc., Monmouth Junction, NJ (US)

( * ) Notice: This patent is subject to a terminal disclaimer.

(21) Appl. No.: 10/992,639

(22) Filed: Nov. 19, 2004

Related U.S. Patent Documents

Reissue of:
(64) Patent No.: 6,492,144
Issued: Dec. 10, 2002
Appl. No.: 09/634,732
Filed: Aug. 3, 2000

U.S. Applications:
(63) Continuation-in-part of application No. 09/609,162, filed on Jul. 3, 2000, now Pat. No. 6,287,820, and a division of application No. 09/609,162, which is a continuation-in-part of application No. 09/230,704, filed on Feb. 4, 2000, now Pat. No. 6,251,638, and a division of application No. 09/230,704, filed as application No. PCT/US98/10965 on May 29, 1998.
(60) Provisional application No. 60/048,170, filed on May 30, 1997, and provisional application No. 60/048,381, filed on Jun. 3, 1997.

(51) Int. Cl.

| | |
|---|---|
| ***C12P 19/34*** | (2006.01) |
| ***C12Q 1/68*** | (2006.01) |
| ***G01N 33/00*** | (2006.01) |
| ***C07H 21/02*** | (2006.01) |
| ***C07H 21/04*** | (2006.01) |

(52) U.S. Cl. ..... 435/91.2; 435/6; 435/91.1; 436/94; 536/23.1; 536/24.3; 536/24.33

(58) Field of Classification Search ..... 435/6, 435/7.21, 7.22, 7.23, 7.31, 7.32, 91.1, 91.2, 435/91.21, 91.32, 91.81; 436/94; 536/23.1, 536/23.72, 23.74, 24.3, 24.33, 25.3
See application file for complete search history.

(56) References Cited

U.S. PATENT DOCUMENTS

| | | | | |
|---|---|---|---|---|
| 4,673,637 A | | 6/1987 | Hyman | 435/34 |
| 4,935,342 A | | 6/1990 | Seligson et al. | 435/6 |
| 5,283,175 A | | 2/1994 | Weaver et al. | 435/6 |
| 5,494,810 A | * | 2/1996 | Barany et al. | 435/91.52 |
| 5,534,413 A | * | 7/1996 | Lo et al. | 435/7.32 |
| 5,770,366 A | | 6/1998 | Bogdahn et al. | 435/6 |
| 5,808,041 A | | 9/1998 | Padhye et al. | 536/25.4 |
| 6,020,124 A | | 2/2000 | Sorenson | 435/6 |
| 6,251,638 B1 | * | 6/2001 | Umansky et al. | 435/91.2 |
| 6,287,820 B1 | * | 9/2001 | Umansky et al. | 435/91.1 |

FOREIGN PATENT DOCUMENTS

WO WO 98/15648 4/1998

OTHER PUBLICATIONS

1988 Stratagene Catalog, p. 39. Published by Stratgene, 11011 North Torrey Pine Road, La Jolla, CA 92037.*

Cottler–Fox et al., Documentation of allogeneic marrow engraftment by DNA analysis of urinary leucocytes. Br. J. Haematol., 79, 122–123, 1991.*

A. Bedi et al., "Association of BK virus with failure of prophylaxis against homorrhagic cystitis following bone marrow transplantation"; *J. Clin. Oncol.* (1995) 13(5). 1103–9.

DIALOG computer database search, "Literature regarding bladder cancer diagnosis through urinalysis" (1996).

HMM. Schatzki; "Detection by CPR of human polyomavirusus BK and JC in immunocompromised individuals and partial sequencing of control regions"; *Journal of Medical Virology,* (193) 42: 138–145.

Kogan, et al., "An improved method for prenatal diagnosis of genetic diseases of analysis of amplified DNA sequences", *New Engl. J. Med.,* (1987) 317(1G): 985–990.

Lisby et al.; Polymerase chain reaction as a rapid diagnostic assay for cytomegalovirus infection renal transplant patients: APMIS, 102, 690–694, 1994.

Lo et al.; "Prenatal sex determination by DNA amplification from maternal peripheral blood", *Lancet,* (1989) 2: 1363–1365.

Mao et al., "Molecular detection of primary bladder cancer by microsatellite analysis"; *Science* (1996) 271: 659–662.

MEDLINE patent database search, "Genetic testing of DNA from urine" (1996).

Nakahori et al. "A human Y–chromosome specific repeated DNA family (DYZ1) consists of a tandem array of pentanucleotides", *Nucleic Acids Res.* (1986) 14(19):7569–7580.

(Continued)

*Primary Examiner*—Frank Lu
(74) *Attorney, Agent, or Firm*—Ivor R. Elrifi, Esq.; Mintz Levin Cohn Ferris Glovsky and Popeo PC

(57) ABSTRACT

Described are non-invasive methods of detecting the presence of specific nucleic acid sequences as well as nucleic acid modifications and alterations by analyzing urine samples for the presence of transrenal nucleic acids. More specifically, the present invention encompasses methods of detecting specific fetal nucleic acid sequences and fetal sequences that contained modified nucleotides by analyzing maternal urine for the presence of fetal nucleic acids. The invention further encompasses methods of detecting specific nucleic acid modifications for the diagnosis of disease, such as cancer and pathogen infections, and detection of genetic predisposition to various disease. The invention specifically encompasses methods of analyzing specific nucleic acid modifications for the monitoring of cancer treatment. The invention further encompasses methods of analyzing specific nucleic acids in urine to track the success of transplanted cells, tissues and organs. The invention also encompasses methods for evaluating the effects of environmental factors and aging on the genome.

136 Claims, 9 Drawing Sheets

OTHER PUBLICATIONS

P.K.S Chan et al.; "Association between polyomaviruria and microscopic haematuris in bone marrow transplant recipients"; *Journal of Infection* (1994) 29:139–146.
S. Porsche; "Monitoring of patients for cytomegalovirus after organ transplantation by centrifugation culture and CPR". *Journal of Medical Virology* (1992), 38:246–251.
Schatzl et al.; "Detection by PCR of human polyomaviruses BK and JC in immunocompromised individuals and partial sequencing of control regions"; *J. Med. Virology,* 42, 138–145, 1994.
Schatzl et al.; "Detection by PCR of human polyomaviruses BK and JC in immunocompromised individuals and partial sequencing of control regions": *Journal of Medical Virology* (1993) 42:138–145.
V. Nickeleit et al., "Polyomavirus infection of renal allograft recipients: from latent infection to manifest disease". *Journal of the American Society of Nephrology* (1999), 10(5): 12 pages.
Vonsover et al., "Detection of CMV in urine comparison between DNA–DNA hybridization, virus isolation and immunoelectronic microscophy"; *J. Viro. Methods,* (1987) 16. 29–37.
Afzal et al. *J. Med. Virol.,* 52:349–353 (1997).
Ahmed et al. *J. Pediatr.,* 131(3):393–397 (1997).
Bayer et al. *Infection,* 24(5):347–353 (1996).
Bessho et al. *J. Otolaryngol Jpn.,* in Japanese, English abstract only, 97(6):1019–1027 (1994).
Böhme et al. *Kretschmer V. Stangel W. Wiebecke D* (*eds.*), Transfusionsmedizin 1991/92, in German, English abstract only, 30:96–99 (1992).
Boom et al. *J. Clin. Microbiol.,* 28(3):495–503 (1990).
Boriskin et al. *J. Virol. Meth.,* 42(1):23–32 (1993).
Burgener–Kairuz et al. *J. Clin. Microbiol.,* 32(8):1902–1907 (1994).
Caldwell et al. *Liver Transplant Surg.,* 2(2):124–129 (1996).
Chang et al. *J. Virol. Meth.,* 58:131–136 (1996).
Dawson et al. *Arch. Pathol. Lab. Med.,* 117(5):511–514 (1993).
Del Portillo et al. *J. Clin. Microbiol.,* 29(10):2163–2168 (1991).
Di Bisceglie et al. *J. Med. Virol.,* 16(4):337–341 (1985).
Echavarria et al. *J. Clin. Microbiol.,* 36(11):3323–3326 (1998).
Fagan et al. *J. Med. Virol.,* 20(2):183–188 (1986).
Frazier et al. *Annals of the New York Academy of Science,* 590:445–458 (1990).
Frazier et al. *Acta Virol.,* 36:83–89 (1992).
Goodman et al. *Infect. Immun.,* 59(1):269–278 (1991).
Halonen et al. *J. Clin. Microbiol.,* 33(3):648–653 (1995).
Harding et al. *Nucl. Acids Res.,* 17(17):6947–6958 (1989).
Harju et al. *Mol. Cell. Probes,* 4(3):223–235 (1990).
Hashinaka et al. *J. Clin. Microbiol.,* 32(3):819–822 (1994).
Hofmeister et al. *Am. J. Trop. Med. Hyg.,* 60(4):598–609 (1999).
Huppertz et al. *Eur. J. Pediatr.,* 152(5):414–417 (1993).
Ieven et al. *Clin. Microbiol. Rev.,* 10(2):242–256 (1997).
Karayiannis et al. *Brit. Med. J.,* 290(6485):1853–1855 (1985).
Karch et al. *J. Clin. Microbiol.,* 32(9):2312–2314 (1994).
Karch et al. *Rheumatol. Int.,* 12(6):227–229 (1993).
Koch et al. *J. Clin. Microbiol.,* 28(1):65–69 (1990).
Kolk et al. *J. Clin. Microbiol.,* 30(10):2567–2575 (1992).
Kox et al. *Neurology,* 45(12):2228–2232 (1995).
Landau et al. *J. Med. Virol.,* 44(3):229–233 (1994).
Lebech et al. *J. Clin. Microbiol.,* 30(7):1646–1653 (1992).
Liebling et al. *Arthr. Rheum.,* 36(5):665–675 (1993).
Lurain et al. *J. Clin. Microbiol.,* 24(5):724–730 (1986).
Maiwald et al. *Eur. J. Clin. Microbiol. Infect. Dis.,* 14(1):25–33 (1995).
Maiwald et al. *Infection,* 23(3):173–179 (1995).
Malloy et al. *J. Clin. Microbiol.,* 28(6):1089–1093 (1990).
McGuire et al. *Pathobiol.,* 60(3):163–167 (1992).
Mercier et al. *Mol. Cell. Probes,* 11:89–94 (1997).
Muncan et al. *J. Urol.,* 156(1):154–156 (1996).
Murdoch et al. *Clin. Infect. Dis.,* 23(3):475–480 (1996).
Kaufman et al. *J. Vet. Diagn. Invest.,* 5:548–554 (1993).
Nielsen et al. *Mol. Cell. Probes,* 4(1):73–79 (1990).
Nogales et al. *Arch Bronconeumol.,* in Spanish, English abstract only, 30:181–184 (1994).
Priem et al. *J. Clin. Microbiol.,* 35(3):685–690 (1997).
Ray et al. *J. Virol. Meth.,* 52:247–263 (1995).
Reddy et al. *Mol. Cell. Probes,* 7:121–126 (1993).
Sakuma et al. *Bone Marrow Transpl.,* 19:49–53 (1997).
Schmidt et al. *Diagn. Microbiol. Infect. Dis.,* 21:121–128 (1995).
Schmidt et al. *J. Clin. Microbiol.,* 34(6):1359–1363 (1996).
Schuster et al. *Monatsschr. Kinderheilkd,* in German, English abstract only, 138:392–394 (1990).
Seesod et al. *J. Clin. Microbiol.,* 31(10):2715–2719 (1993).
Sexton et al. *Am. J. Trop. Med. Hyg.,* 50(1):59–63 (1994).
Weiland et al. *Kretschmer V . Stangel W. Wiebecke D* (*eds.*), Transfusionsmedizin 1991/92, in German, English abstract only, 30:92–95 (1992).
Wilborn et al. *J. Med. Virol.,* 47(1):65–69 (1995).
Williams et al. *DNA Cell Biol.,* 11(3):207–213 (1992).
Zambardi et al. *Mol. Cell. Probes,* 9:91–99 (1995).

* cited by examiner

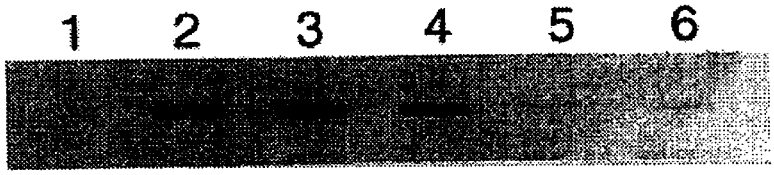
Figure 7
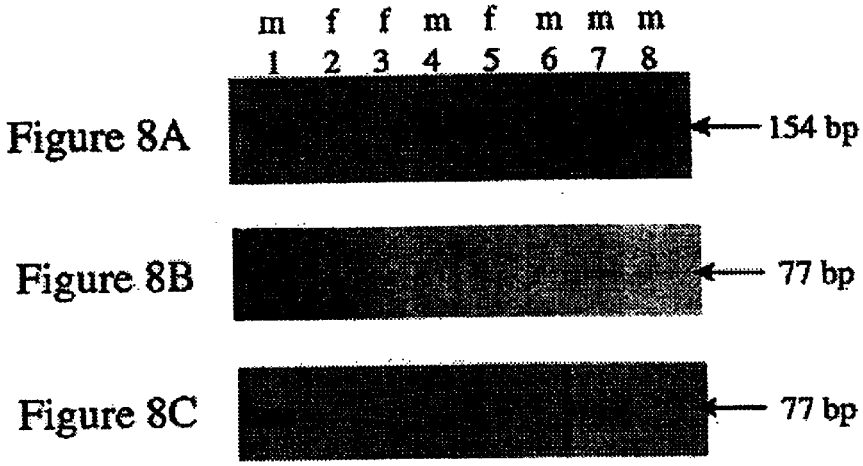

METHODS FOR DETECTION OF NUCLEIC ACID SEQUENCES IN URINE

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part and a division of application Ser. No. 09/609,162 filed Jul. 3, 2000, now U.S. Pat. No. 6,287,820, which is a continuation-in-part and a division of application Ser. No. 09/230,704, filed Feb. 4, 2000, now U.S. Pat. No. 6,251,704, which is the United States national phase of International Patent Application No. PCT/US98/10965, filed May 29, 1998, which claims priority of U.S. provisional patent applications No. 60/058,170, filed May 30, 1997, and Ser. No. 60/048,381, filed Jun. 3, 1997.

STATEMENT OF RIGHTS TO INVENTIONS MADE UNDER FEDERALLY SPONSORED RESEARCH (Not Applicable)

TECHNICAL FIELD

The present invention encompasses non-invasive methods of detecting the presence of specific nucleic acid sequences as well as nucleic acid modifications and alterations by analyzing urine samples for the presence of transrenal nucleic acids. More specifically, the present invention encompasses methods of detecting specific fetal nucleic acid sequences and fetal sequences that contained modified nucleotides by analyzing maternal urine for the presence of fetal nucleic acids. The invention further encompasses methods of detecting specific nucleic acid modifications for the diagnosis of diseases, such as cancer and pathogen infections, and detection of genetic predisposition to various diseases. The invention specifically encompasses methods of analyzing specific nucleic acid modifications for the monitoring of cancer treatment. The invention further encompasses methods of analyzing specific nucleic acids in urine to track the success of transplanted cells, tissues and organs. The invention also encompasses methods for evaluating the effects of environmental factors and aging on the genome.

BACKGROUND

Human genetic material is an invaluable source of information. Over the last several decades, scientific endeavors have developed many methods of analyzing and manipulating this genetic material (nucleic acids, DNA and RNA) for a variety of uses. These applications of molecular biology have been at the heart of numerous modern medical techniques for diagnosis and treatment. Thus, means of obtaining, isolating and analyzing this genetic material has become of foremost importance.

Until now, the fragile nature of nucleic acids, and their location encapsulated within cells, made the acquisition of genetic material for diagnosis in certain cases necessarily intrusive. For example, tumor diagnosis often requires surgery to obtain tumor cells. Similarly, doctors perform amniocenteses to obtain fetal DNA for a variety of diagnostic uses. This procedure requires the insertion of a needle through the abdomen of a pregnant woman and into the amniotic sac. Such intrusive practices carry with them a level of risk to both the fetus and the mother. While developments in ultrasound have contributed less intrusive alternative methods of fetal monitoring during pregnancy, these methods are not appropriate for diagnosing certain genetic defects and are not effective during the early stages of pregnancy, even for determining fetal sex.

Recent studies into the various mechanisms and consequences of cell death have opened a potential alternative to the invasive techniques described above. It is well established that apoptotic cell death is frequently accompanied by specific internucleosomal fragmentation of nuclear DNA. However, the fate of these chromatin degradation products in the organism has not been investigated in detail.

Based on the morphology of dying cells, it is believed that there exist two distinct types of cell death, necrosis and apoptosis. Kerr, J. F. et al., Br. J. Cancer 26:239-257, (1972). Cell death is an essential event in the development and function of multicellular organisms. In adult organisms, cell death plays a complementary role to mitosis in the regulation of cell populations. The pathogenesis of numerous diseases involves failure of tissue homeostasis which is presumed to be linked with cytotoxic injury or loss of normal control of cell death. Apoptosis can be observed during the earliest stages of embryogenesis in the formation of organs, substitution of one tissue by another and resorption of temporary organs.

Necrosis is commonly marked by an early increase in total cell volume and subcellular organelle volume followed by autolysis. Necrosis is considered to be a catastrophic metabolic failure resulting directly from severe molecular and/or structural damage. Apoptosis is an atraumatic programmed cell death that naturally occurs in the normal development and maintenance of healthy tissues and organs. Apoptosis is a much more prevalent biological phenomenon than necrosis. Kerr, J. F. et al., Br. J. Cancer 26:239-257, (1972). Umansky, S. Molecular Biology (Translated from Molekulyarnaya Biologiya) 30:285-295, (1996). Vaux, D. L. et al., Proc Natl Acad Sci USA. 93:2239-2244, (1996). Umansky, S., J. Theor. Biol. 97:591-602, (1982). Tomei, L. D. and Cope, F. D. Eds., Apoptosis: The Molecular Basis of Cell Death, Cold Spring Harbor Laboratory Press, Cold Spring Harbor, N.Y., (1991).

Apoptosis is also a critical biological function which occurs naturally during embryogenesis, positive and negative selection of T and B-lymphocytes, glucocorticoid induced lymphocyte death, death induced by radiation and temperature shifts, and death following deprivation of specific growth factors. In addition, apoptosis is an important part of an organism's defense against viral infection. Apoptosis has been observed in preneoplastic foci found in the liver following tumor promoter phenobarbital withdrawal, in involuting hormone-dependent tissues and in tumors upon hormone withdrawal. Many antitumor drugs, including inhibitors of topoisomerase II as well as tumor necrosis factors induce apoptotic cell death. Apoptotic cell death is characterized by morphologic changes such as cellular shrinkage, chromatin condensation and margination, cytoplasmic blebbing, and increased membrane permeability. Gerschenson et al. (1992) FASEB J. 6:2450-2455; and Cohen and Duke (1992) Ann. Rev. Immunol. 10:267-293. Specific internucleosomal DNA fragmentation is a hallmark for many, but notably not all, instances of apoptosis.

In necrotic cells, DNA is also degraded but as a result of the activation of hydrolytic enzymes, generally yielding mono- and oligonucleotide DNA products. Afanasyev, V. N. et al., FEBS Letters. 194: 347-350 (1986).

Recently, earlier stages of nuclear DNA degradation have been described. It was shown that after pro-apoptotic treatments, DNA cleavage begins with the formation of high molecular weight DNA fragments in the range of 50-300 kilobases, the size of DNA found in chromosome loops. Walker, P. R. et al., Cancer Res. 51:1078-1085 (1991). Brown, D. G. et al., J. Biol. Chem. 268:3037-3039 (1993). These large fragments are normally degraded to nucleosomes and their oligomers. However, in some cases of apoptotic cell death only high molecular weight DNA fragments can be observed. Oberhammer, F. et al., EMBO J. 12:3679-3684 (1993). There are also data on the appearance of such fragments in some models of necrotic cell death. Kataoka, A. et al., FEBS Lett. 364:264-267 (1995).

Available data on the fate of these chromatin degradation products in organisms provide little guidance. Published results indicate that only small amounts of DNA can be detected in blood plasma or serum. Fournie, G. J. et al., Gerontology 39:215-221 (1993). Leon, S. et al., Cancer Research 37:646-650 (1977). It can be difficult to ensure that this DNA did not originate from white blood cells as a result of their lysis during sample treatment.

Extracellular DNA with microsatellite alterations specific for small cell lung cancer and head and neck cancer was found in human serum and plasma by two groups. Chen, X. Q. et al., Nature Medicine 2:1033-1035 (1996). Nawroz, H. et al., Nature Medicine 2:1035-1037 (1996). Others have proposed methods of detecting mutated oncogene sequences in soluble form in blood. U.S. Pat. No. 5,496,699, to George D. Sorenson. However, the use of blood or plasma as a source of DNA is both intrusive to the patient and problematic for the diagnostic technician. In particular, a high concentration of proteins (about 100 mg/ml) as well as the presence of compounds which inhibit the polymerase chain reaction (PCR) make DNA isolation and analysis difficult.

A few groups have identified, by PCR, DNA modifications or viral infections in bodily fluids, including urine. Ergazaki, M., et al., "Detection of the cytomegalovirus by the polymerase chain reaction, DNA amplification in a kidney transplanted patient," In Vivo 7:531-4 (1993); Saito, S., "Detection of H-ras gene point mutations in transitional cell carcinoma of human urinary bladder using polymerase chain reaction," Keio J Med 41:80-6 (1992). Mao, L., et al., "Molecular Detection of Primary Bladder Cancer by Microsatellite Analysis," Science 271:659-662 (1996). The DNA that these groups describe detecting is from kidney cells or cells lining the bladder. When detecting a viral infection, many viruses infect cells of the bladder, thereby obtaining entry into the urine. The descriptions do not teach methods of detecting DNA sequences in urine that do not originate from the bladder or kidney cells, and thus would not include DNA that passes through the kidney barrier and remains in detectable form in urine prior to detection.

What is needed is a non-invasive method of obtaining nucleic acid samples from cells located outside the urinary tract, for use in diagnostic and monitoring applications. The ability to obtain, in a non-invasive way, and analyze specific nucleic acid sequences would have value for purposes including, but not limited to, determining the sex of a fetus in the early stages of development, diagnosing fetal genetic disorders, and achieving early diagnosis of cancer. The presence of Y chromosome gene sequence in the urine of a pregnant woman would be indicative of a male fetus. The presence of gene sequences specific to a certain type of tumor in the urine of a patient would be a marker for that tumor. Thus, such methods would be useful in suggesting and/or confirming a diagnosis.

Methods for analysis of transrenal nucleic acids and are in urine have not been previously described.

All references cited herein are incorporated by reference in their entirety.

SUMMARY OF THE INVENTION

The present invention encompasses non-invasive methods of detecting the presence of specific nucleic acid sequences as well as nucleic acid modifications and alterations by analyzing urine samples for the presence of transrenal nucleic acids. More specifically, the present invention encompasses methods of detecting specific fetal nucleic acid sequences and fetal sequences that contained modified nucleotides by analyzing maternal urine for the presence of fetal nucleic acids. The invention further encompasses methods of detecting specific nucleic acid modifications for the diagnosis of diseases, such as cancer and pathogen infections, and detection of genetic predisposition to various diseases. The invention specifically encompasses methods of analyzing specific nucleic acid modifications for the monitoring of cancer treatment. The invention further encompasses methods of analyzing specific nucleic acids in urine to track the success of transplanted cells, tissues and organs. The invention also encompasses methods for evaluating the effects of environmental factors and aging on the genome.

The present invention encompasses methods of analyzing a fragment of fetal DNA that has crossed the placental and kidney barriers, comprising: obtaining a urine sample, suspected of containing fetal polymeric transrenal nucleic acids, from a pregnant female; and assaying for the presence of said fetal polymeric DNA in said urine sample.

The target fetal DNA sequence can be, for example, a sequence that is present only on the Y chromosome. The step of assaying for the presence of unique fetal DNA sequence can be performed using one or more of a variety of techniques, including, but not limited to, hybridization, cycling probe reaction, cleavage product detection, polymerase chain reaction, nested polymerase chain reaction, polymerase chain reaction-single strand conformation polymorphism, ligase chain reaction, strand displacement amplification and restriction fragments length polymorphism. The step of performing the polymerase chain reaction can comprise using primers substantially complementary to a portion of the unique fetal DNA sequence, and the unique fetal DNA sequence can be a sequence that is present in the paternal genome and not present in the maternal genome.

The present invention further encompasses methods having the step of reducing DNA degradation in the urine sample. Reducing DNA degradation can be by treatment with compounds selected from the group consisting of: ethylenediaminetetraacetic acid, guanidine-HCl, Guanidine isothiocyanate, N-lauroylsarcosine, and Na-dodecylsulphate. DNA degradation can further be reduced by taking a urine sample that has been held in the bladder less than 12 hours.

The present invention encompasses methods where DNA in the urine sample is substantially isolated prior to assaying for the presence of a unique fetal DNA sequence in the urine sample. Substantial isolation can be by, but is not limited to, precipitation and adsorption on a resin.

In one embodiment of the present invention, the presence of the particular unique fetal DNA sequence is indicative of a genetic disease.

In some cases, it can be desirable to filter the urine sample to remove contaminating nucleic acids before assaying. In a specific embodiment, the filtering removes DNA comprising more than about 1000 nucleotides.

The present invention also encompasses methods of analyzing a target nucleic acid sequence in urine, comprising: providing a urine sample; and assaying the urine sample for the presence of a target DNA sequence that has crossed the kidney barrier.

The step of assaying for the presence of a target DNA sequence can be selected from the group consisting of hybridization, cycling probe reaction, polymerase chain reaction, nested polymerase chain reaction, polymerase chain reaction-single strand conformation polymorphism, ligase chain reaction, strand displacement amplification and restriction fragments length polymorphism. The step of assaying for the presence of a target DNA sequence can comprise techniques for amplifying the target DNA.

In one embodiment, the target DNA sequence comprises an altered gene sequence, and that altered gene sequence can comprise a modification occurring in tumor cells in specific.

The present invention further encompasses methods having the step of reducing DNA degradation in the urine sample prior to assaying the urine sample for the presence of a target DNA sequence that has crossed the kidney barrier. Reducing DNA degradation can be by treatment with compounds selected from the group consisting of: ethylenediaminetetraacetic acid, guanidine-HCl, Guanidine isothiocyanate, N-lauroylsarcosine, and Na-dodecylsulphate. DNA degradation can further be reduced by taking a urine sample that has been held in the bladder less than 12 hours.

The present invention encompasses methods where DNA in the urine sample is substantially isolated prior to assaying for the presence of a target DNA sequence that has crossed the kidney barrier. Substantial isolation can be by, but is not limited to, precipitation and adsorption on a resin.

In some cases, it is desirable to filter the urine sample to remove contaminating nucleic acids before assaying for the presence of a target DNA sequence that has crossed the kidney barrier. In a specific embodiment, the filtering removes DNA comprising more than about 1000 nucleotides.

The present invention also encompasses methods of analyzing a target nucleic acid sequence in urine, comprising: providing a urine sample, suspected of containing DNA that has crossed the kidney barrier, from a patient; amplifying a target DNA sequence in the DNA that has crossed the kidney barrier, comprising using a primer substantially complementary to a portion of the target DNA sequence that does not occur in cells of the urinary tract of the patient, to make amplified target DNA; and detecting the presence of the amplified target DNA. Amplification can comprise performing a polymerase chain reaction. The target DNA sequence can comprise an altered gene sequence, such as a modification occurring in tumor cells.

The present invention further encompasses methods having the step of reducing DNA degradation in the urine sample prior to amplifying a target DNA sequence in the DNA that has crossed the kidney barrier. Reducing DNA degradation can be by treatment with compounds selected from the group consisting of: ethylenediaminetetraacetic acid, guanidine-HCl, Guanidine isothiocyanate, N-lauroylsarcosine, and Na-dodecylsulphate. DNA degradation can further be reduced by taking a urine sample that has been held in the bladder less than 12 hours.

The present invention encompasses methods where DNA in the urine sample is substantially isolated prior to amplifying a target DNA sequence in the DNA that has crossed the kidney barrier. Substantial isolation can be by, but is not limited to, precipitation and adsorption on a resin.

In some cases, it can be desirable to filter the urine sample to remove contaminating nucleic acids before amplifying a target DNA sequence in the DNA that has crossed the kidney barrier. In a specific embodiment, filtering removes DNA comprising more than about 1000 nucleotides.

The present invention further encompasses a method of determining the sex of a fetus, comprising: obtaining a urine sample, suspected of containing fetal male DNA, from a pregnant female; amplifying a portion of the male DNA present in the urine sample by the polymerase chain reaction, using an oligodeoxynucleotide primer having sequences specific to a portion of the Y chromosome, to produce amplified DNA; and detecting the presence of the amplified DNA.

The present invention encompasses a diagnostic kit for detecting the presence of human male fetal DNA in maternal urine, comprising: reagents to facilitate the isolation of DNA from urine; reagents to facilitate amplification of DNA by the polymerase chain reaction; a heat stable DNA polymerase; and an oligodeoxynucleotide specific for a sequence only occurring on the Y chromosome.

Additionally, the present invention encompasses oligonucleotide primers for the amplification of sequences of the Y chromosome, comprising SEQ ID NO: 3 and SEQ ID NO: 4. A kit for detecting male nucleic acid is also encompasses, this pair of primers. The invention also encompasses a method for detecting Y-chromosome nucleic acid, comprising: carrying out a polymerase chain reaction using these primers and detecting amplified Y-chromosome nucleic acid.

Oligonucleotide probes are also disclosed, including SEQ ID NO: 3 and SEQ ID NO: 4, which can be used for the detection of male nucleic acid.

The present invention further encompasses methods of detecting cancer in a patient, comprising: providing a urine sample from a patient; and analyzing said urine sample for a nucleic acid sequence, indicative of cancer, that has crossed the kidney barrier. In a specific embodiment, said step of analyzing for the presence of said nucleic acid sequence is selected from the group consisting of hybridization, cycling probe reaction, polymerase chain reaction, nested polymerase chain reaction, polymerase chain reaction-single strand conformation polymorphism, ligase chain reaction, strand displacement amplification and restriction fragments length polymorphism. In another embodiment, analyzing for the presence of said nucleic acid sequence comprises amplifying said nucleic acid sequence indicative of cancer.

In another specific embodiment, said analyzing comprises quantifying the number of copies of said nucleic acid sequence.

In one embodiment said nucleic acid sequence contains an anomaly indicative of colon cancer. In another embodiment, said nucleic acid sequence contains mutant K-ras DNA.

It is helpful in some embodiments to include a step to reduce DNA degradation in said urine sample, which in one embodiment encompasses treatment with a compound selected from the group comprising: ethylenediaminetetraacetic acid, guanidine-HCl, Guanidine isothiocyanate, N-lauroylsarcosine, and Na-dodecylsulphate.

In another embodiment the urine sample has been held in the bladder less than 12 hours.

In one embodiment, it is beneficial to substantially isolate said nucleic acid sequence prior to assaying the urine for the presence of a nucleic acid sequence, indicative of cancer, that has crossed the kidney barrier. In alternate embodiments, the nucleic acid sequence is substantially isolated by precipitation or by treatment with a solid adsorbent material. In another embodiment, the urine sample is filtered to remove contaminants, and, in a specific embodiment, the filtering removes DNA comprising more than about 1000 nucleotides.

Also encompassed by the present invention is a method of monitoring transplanted material in a patient, comprising: providing a urine sample suspected of containing nucleic acid from transplanted material; and analyzing said urine sample for a nucleic acid sequence that has crossed the kidney barrier and that was not present in the patient prior to transplantation. In a specific embodiment, the nucleic acid sequence is not present in cells of the urinary tract of said patient.

In a specific embodiment, the analyzing comprises amplifying said nucleic acid sequence with a primer substantially complementary to a part of said nucleic acid sequence that does not occur in cells of the urinary tract of the patient, to make amplified target DNA, and detecting the presence of said amplified target DNA. More specifically, the amplifying can comprise performing a polymerase chain reaction.

In another specific embodiment is included the additional step of reducing DNA degradation in said urine sample, which can be performed in any way known, but, without limitation, includes situations wherein reducing DNA degradation is by treatment with a compound selected from the group consisting of: ethylenediaminetetraacetic acid, guanidine-HCl, Guanidine isothiocyanate, N-lauroylsarcosine, and Na-dodecylsulphate.

In some embodiments, said urine sample has been held in the bladder less than 12 hours.

It is desirable in some embodiments to substantially isolate said nucleic acid sequence. In alternate embodiments, the nucleic acid sequence is substantially isolated by precipitation, and/or by adsorption on a resin.

Additionally, one can filter the urine sample to remove contaminants. In a specific embodiment, this filtering removes DNA comprising more than about 1000 nucleotides.

In yet another embodiment a method of monitoring cancer treatment in a patient is encompassed, comprising: providing a urine sample from a patient; and analyzing said urine sample for the quantity of a nucleic acid sequence, indicative of cancer, that has crossed the kidney barrier.

Further encompassed by the present invention is a diagnostic kit for detecting a genetic mutation indicative of cancer in the DNA of a patient, comprising: reagents to facilitate the isolation of DNA from urine; reagents to facilitate amplification of DNA by the polymerase chain reaction; a heat stable DNA polymerase; and an oligodeoxynucleotide specific for a sequence only occurring in a genetic mutation characteristic of cancer.

Also encompassed by the present invention is a diagnostic kit for detecting DNA from a transplanted material in the urine of a patient, comprising: reagents to facilitate the isolation of DNA from urine; reagents to facilitate amplification of DNA by the polymerase chain reaction; a heat stable DNA polymerase; and an oligodeoxynucleotide specific for a sequence that occurs in the transplanted material, and did not occur in the patient prior to transplantation.

BRIEF DESCRIPTION OF THE DRAWINGS

FIG. 7 is an autoradiograph of a Zeta-probe membrane which depicts the detection, by hybridization, of specific Y chromosome DNA sequences in urine samples from pregnant women. Lanes: 1—negative control (non-pregnant female); 2—positive control (male total genome DNA, 5 ng); 3,4—male fetuses; 5,6—female fetuses.

FIGS. 8A, 8B, and 8C are photographs of agarose gels which compare fetal DNA to maternal urine DNA at gestation ages of approximately 7-8 weeks. FIG. 8A represents fetal DNA, FIG. 8B represents maternal urine DNA prepared by simple 10-fold urine dilution, and FIG. 8C represents maternal urine DNA prepared by GEAE Sephadex A-25 adsorption M-male; f-female.

DETAILED DESCRIPTION OF THE INVENTION

Figure 1A:
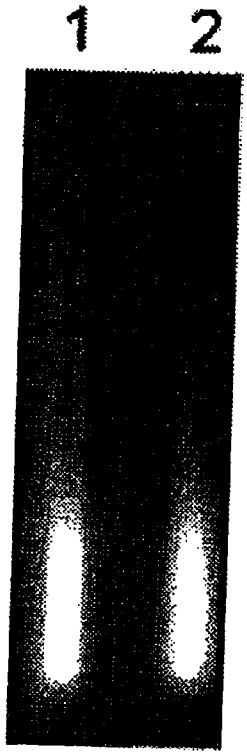
FIG. 1A is a photograph of an agarose gel, stained with ethidium bromide, which depicts the detection of polymeric DNA in urine samples taken from mice injected with λ phage DNA. The results of two experiments (lanes 1 and 2) are presented.

The present invention is based on the new discovery that genetic material from cells in the body can pass through the kidney barrier and appear in the urine of a mammal in a form sufficiently intact to be analyzed. In addition, genetic material from cells of the developing embryo can cross both the placental and kidney barriers and appear in the pregnant mother's urine. The present invention encompasses non-invasive methods of detecting the presence of specific nucleic acid sequences as well as nucleic acid modifications and alterations by analyzing urine samples for the presence of transrenal nucleic acids. More specifically, the present invention encompasses methods of detecting specific fetal nucleic acid sequences and fetal sequences that contained modified nucleotides by analyzing maternal urine for the presence of fetal nucleic acids. The invention further encompasses methods of detecting specific nucleic acid modifications for the diagnosis of diseases, such as cancer and pathogen infections, and detection of genetic predisposition to various diseases. The invention specifically encompasses methods of analyzing specific nucleic acid modifications for the monitoring of cancer treatment. The invention further encompasses methods of analyzing specific nucleic acids in urine to track the success of transplanted cells, tissues and organs. The invention also encompasses methods for evaluating the effects of environmental factors and aging on the genome.

This invention further encompasses novel primers, YZ1 and YZ2, for use in amplification techniques of the present invention, as set forth in Example 3, below.

The methods of the present invention offer improvements over previous methods of diagnosis, detection and monitoring due to their inherently non-invasive nature.

To facilitate understanding of the invention, a number of terms are defined below.

The term "gene" refers to a DNA sequence that comprises control and coding sequences necessary for the transcription of an RNA sequence. The term "genome" refers to the complete gene complement of an organism, contained in a set of chromosomes in eukaryotes.

A "wild-type" gene or gene sequence is that which is most frequently observed in a population and is thus arbitrarily designed the "normal" or "wild-type" form of the gene. In contrast, the term "modified", "mutant", "anomaly" or "altered" refers to a gene, sequence or gene product which displays modifications in sequence and or functional properties (i.e., altered characteristics) when compared to the wild-type gene, sequence or gene product. For example, an altered sequence detected in the urine of a patient can display a modification that occurs in DNA sequences from tumor cells and that does not occur in the patient's normal (i.e. non cancerous) cells. It is noted that naturally-occurring mutants can be isolated; these are identified by the fact that they have altered characteristics when compared to the wild-type gene or gene product. Without limiting the invention to the detection of any specific type of anomaly, mutations can take many forms, including addition, addition-deletion, deletion, frame-shift, missense, point, reading frame shift, reverse, transition and transversion mutations as well as microsatellite alterations.

A "disease associated genetic anomaly" refers to a gene, sequence or gene product that displays modifications in sequence when compared to the wild-type gene and that is indicative of the propensity to develop or the existence of a disease in the carrier of that anomaly. A disease associated genetic anomaly encompasses, without limitation, inherited anomalies as well as new mutations.

The term "unique fetal DNA sequence" is defined as a sequence of nucleic acids that is present in the genome of the fetus, but not in the maternal genome.

The terms "oligonucleotide" and "polynucleotide" and "polymeric" nucleic acid are interchangeable and are defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide can be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends.

When two different, non-overlapping oligonucleotides anneal to different regions of the same linear complementary nucleic acid sequence, and the 3' end of one oligonucleotide points towards the 5' end of the other, the former can be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" can occur naturally, as in a purified restriction digest or be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment can be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

A "target" nucleic acid is a nucleic acid sequence to be evaluated by hybridization, amplification or any other means of analyzing a nucleic acid sequence, including a combination of analysis methods.

"Hybridization" methods involve the annealing of a complementary sequence to the target nucleic acid (the sequence to be analyzed). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Hybridization encompasses, but is not limited to, slot, dot and blot hybridization techniques.

It is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, could require that the hybridization method distinguish between partial and complete complementarity. It may be of interest to detect genetic polymorphisms.

Methods that allow for the same level of hybridization in the case of both partial as well as complete complementarity are typically unsuited for such applications; the probe will hybridize to both the normal and variant target sequence. The present invention contemplates that for some diagnostic purposes, hybridization be combined with other techniques (such as restriction enzyme analysis). Hybridization, regardless of the method used, requires some degree of complementarity between the sequence being analyzed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Specific bases not commonly found in natural nucleic acids can be included in the nucleic acids of the present invention and include, for example, inosine and 7-deazaguanine. Complementarity need not be perfect; stable duplexes can contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value can be calculated by the equation: $Tm=81.5+0.41(\% G+C)$, when a nucleic acid is in aqueous solution at 1 M NaCl (see e.g., Anderson and Young, Quantitative Filter Hybridisation, in Nucleic Acid Hybridisation (1985). Other references include more sophisticated computations which take structural as well as sequence characteristics into account for the calculation of Tm.

The term "probe" as used herein refers to an oligonucleotide (i.e., a sequence of nucleotides), whether occurring naturally as in a purified restriction digest or produced synthetically, which forms a duplex structure or other complex with a sequence in another nucleic acid, due to complementarity or other means of reproducible attractive interaction, of at least one sequence in the probe with a sequence in the other nucleic acid. Probes are useful in the detection, identification and isolation of particular gene sequences. It is contemplated that any probe used in the present invention will be labeled with any "reporter molecule," so that it is detectable in any detection system, including, but not limited to, enzyme (e.g., ELISA, as well as enzyme-based histochemical assays), fluorescent, radioactive, and luminescent systems. It is further contemplated that the oligonucleotide of interest (i.e., to be detected) will be labeled with a reporter molecule. It is also contemplated that both the probe and oligonucleotide of interest will be labeled. It is not intended that the present invention be limited to any particular detection system or label.

The term "label" as used herein refers to any atom or molecule which can be used to provide a detectable (preferably quantifiable) signal, and which can be attached to a nucleic acid or protein. Labels provide signals detectable by any number of methods, including, but not limited to, fluorescence, radioactivity, colorimetry, gravimetry, X-ray diffraction or absorption, magnetism, and enzymatic activity.

The term "substantially single-stranded" when used in reference to a nucleic acid target means that the target molecule exists primarily as a single strand of nucleic acid in contrast to a double-stranded target which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene can vary in sequence by the presence of single base substitutions and/or deletions or insertions of one or more nucleotides. These two forms of the structural gene are said to vary in sequence from one another. A second mutant form of the structural gene can exit. This second mutant form is said to vary in sequence from both the wild-type gene and the first mutant form of the gene.

The terms "structure probing signature," "hybridization signature" and "hybridization profile" are used interchangeably herein to indicate the measured level of complex formation between a target nucleic acid and a probe or set of probes, such measured levels being characteristic of the target nucleic acid when compared to levels of complex formation involving reference targets or probes.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence can be used in PCRs, RT-PCRs and the like.

"Nucleic acid sequence" as used herein refers to an oligonucleotide, nucleotide or polynucleotide, and fragments or portions thereof, and to DNA or RNA of genomic or synthetic origin which can be single- or double-stranded, and represent the sense or antisense strand.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

A "substitution" results from the replacement of one or more nucleotides or amino acids by different nucleotides or amino acids, respectively.

A "modification" in a nucleic acid sequence refers to any change to a nucleic acid sequence, including, but not limited to a deletion, an addition, an addition-deletion, a substitution, an insertion, a reversion, a transversion, a point mutation, a microsatellite alteration, methylation or nucleotide adduct formation.

As used herein, the terms "purified", "decontaminated" and "sterilized" refer to the removal of contaminant(s) from a sample.

As used herein, the terms "substantially purified" and "substantially isolated" refer to nucleic acid sequences that are removed from their natural environment, isolated or separated, and are preferably 60% free, more preferably 75% free, and most preferably 90% free from other components with which they are naturally associated. An "isolated polynucleotide" is therefore a substantially purified polynucleotide. It is contemplated that to practice the methods of the present invention polynucleotides can be, but need not be substantially purified. A variety of methods for the detection of nucleic acid sequences in unpurified form are known in the art.

"Amplification" is defined as the production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). As used herein, the term "polymerase chain reaction" ("PCR") refers to the method of K. B. Mullis (U.S. Pat. Nos. 4,683,195 and 4,683,202, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "polymerase" refers to any enzyme suitable for use in the amplification of nucleic acids of interest. It is intended that the term encompass such DNA polymerases as Taq DNA polymerase obtained from Thermus aquaticus, although other polymerases, both thermostable and thermolabile are also encompassed by this definition.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity can be "partial," in which only some of the nucleic acids' bases are matched according to the base pairing rules. Or, there can be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There can be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence can be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that are non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding the probe will not hybridize to the second non-complementary target.

Numerous equivalent conditions can be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution can be varied to generate conditions of either low or high stringency hybridization different from, but equivalent to, the above listed conditions. The term "hybridization" as used herein includes "any process by which a strand of nucleic acid joins with a complementary strand through base pairing" (Coombs, Dictionary of Biotechnology, Stockton Press, New York N.Y. [1994].

"Stringency" typically occurs in a range from about Tm-5° C. (5° C. below the Tm of the probe) to about 20° C. to 25° C. below Tm. As will be understood by those of skill in the art, a stringent hybridization can be used to identify or detect identical polynucleotide sequences or to identify or detect similar or related polynucleotide sequences.

As used herein the term "hybridization complex" refers to a complex formed between two nucleic acid sequences by virtue of the formation of hydrogen bonds between complementary G and C bases and between complementary A and T bases; these hydrogen bonds can be further stabilized by base stacking interactions. The two complementary nucleic acid sequences hydrogen bond in an antiparallel configuration. A hybridization complex can be formed in solution (e.g., C0t or R0t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein, the term "antisense" is used in reference to RNA sequences which are complementary to a specific RNA (e.g., mRNA) or DNA sequence. Antisense RNA can be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either further transcription of the mRNA or its translation. In this manner, mutant phenotypes can be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense. A biological sample suspected of containing nucleic acid can comprise, but is not limited to, genomic DNA (in solution or bound to a solid support such as for Southern blot analysis), cDNA (in solution or bound to a solid support), and the like.

The term "urinary tract" as used herein refers to the organs and ducts which participate in the secretion and elimination of urine from the body.

The terms "transrenal DNA" and "transrenal nucleic acid" as used herein refer to nucleic acids that have crossed the kidney barrier.

The present invention encompasses a platform for the detection and gene specific analysis of transrenal DNA fragments carrying different nucleotide lesions and adducts caused by various external and internal DNA modifying factors. Without limiting the scope of the invention, but in the interest of clarity, some factors that generate DNA modifications might be grouped in three classes: (i) physical, including but not limited to gamma and UV irradiation, temperature fluctuations; (ii) chemical, including but not limited to environmental pollutants, naturally occurring genotoxins, carcinogens, anticancer drugs and (iii) reactive metabolites such as active forms of oxygen, lipid peroxidation products and hydrolytic agents.

I. APPLICATIONS OF THE METHODS OF THE PRESENT INVENTION

The present invention can be used for many applications, including, without in any way limiting the invention, the following.

A. Analyzing for the Presence of Fetal Nucleic Acids in Maternal Urine

The present invention provides methods of analyzing for the presence of specific fetal nucleic acid sequences or nucleic acid modifications by detecting specific fetal nucleic acid sequences that have crossed the placental and kidney barriers and are present in maternal urine. The methods generally involve the steps of obtaining a urine sample from a pregnant woman and subjecting the material to a method of detecting a specific fetal nucleic acid sequence or modification of interest. In one embodiment, the method further encompasses substantially purifying nucleic acids present in the urine sample prior to detecting the specific nucleic acid sequence or modification of interest. These methods have a variety of diagnostic applications, including the determination of fetus sex and the identification of fetal genetic diseases, such as those inherited from the father for various purposes, including determinations of paternity.

The inventions described herein can be used, for example, to diagnose any of the more than 3000 genetic diseases currently known or to be identified (e.g. hemophilias, thalassemias, Duchenne muscular dystrophy, Huntington's disease, Alzheimer's disease and cystic fibrosis). Any genetic disease for which the mutation(s) or other modification(s) and the surrounding nucleotide sequence is known can be identified by methods of the present invention. Some diseases may be linked to known variations in methylation of nucleic acids, that can also be identified by methods of the present invention.

Further, there is growing evidence that some DNA sequences can predispose an individual to any of a number of diseases such as diabetes, arteriosclerosis, obesity, various autoimmune diseases and cancer (e.g. colorectal, breast, ovarian, lung), or chromosomal abnormality (either prenatally or postnatally). The diagnosis for a genetic disease, chromosomal aneuploidy or genetic predisposition can be performed prenatally by collecting urine from the pregnant mother.

Urine DNA analysis provides an easier and safer way to perform prenatal testing. A fetus receives equal amount of genetic information from both parents. The loss of a large number of fetal cells during development is a major part of the genetic program for embryonic differentiations and formation of a normal body. DNA from these dying embryonic cells not only escapes into the bloodstream of the mother, but also crosses the kidney barriers where it appears in the mother's urine. As shown in the following examples, pieces of the male-specific Y chromosome can be found in the urine of women pregnant with male fetuses. Example 8, below, shows that the fetal genetic information was found in the mother's urine as early as the 7th to $_{8}^{th}$ week of pregnancy, that is, at least 6-8 weeks earlier than can be obtained by either amniocentesis or chorionic villus sampling.

In one embodiment of this invention, a simple noninvasive test can be used for early determination of the fetal gender. However, there are more far-reaching consequences of these findings with regard to development of modern safe diagnostic techniques. The discovery that DNA from the developing embryo appears in the mother's urine presents the opportunity to quickly develop products for analysis of genes inherited from the father. These include genes that contain disease-related mutations or can cause problems on different genetic backgrounds. As an example, if a pregnant woman is Rh−(negative Rhesus factor) and produces anti-RhD antibodies and a father is Rh+, amniocentesis is currently recommended for early diagnostics of Rh incompatibility, which often causes life threatening hemolytic anemia in the newborn baby. Detection of the RhD gene-specific sequence in the mother's urine will be an excellent alternative to amniocentesis, which is considered hazardous by a growing number of physicians worldwide. This test is also less expensive and more cost-effective, because it avoids the necessity of a surgical step in obtaining samples for analysis.

With the advent of broad-based genetic mapping initiatives such as the Human Genome Project, there is an expanding list of targets and applications for genetic analysis of urine DNA. Many diseases inherited by the fetus will be easily detectable by analysis of the mother's urine DNA. These include Marfan Syndrome, Sickle Cell Anemia, Tay Sachs Disease, and a group of neurodegenerative disorders, including Huntington's Disease, Spinocerebellar Ataxia 1, Machado-Joseph Disease, Dentatorubraopallidoluysian Atrophy, and others that affect the fetus and newborn. Urine DNA analysis can detect the presence of the mutant gene inherited from the father. Also, if the mother's genome bears a mutation, the test can help determine whether a normal version of the gene has been inherited from the father.

In addition to providing answers to commonly asked questions from expectant couples, determination of fetal sex can also be very helpful if there is a risk of X chromosome-linked inherited disease, e.g. Hemophilia or Duchenne Muscular Dystrophy. Again prenatal testing for inherited diseases is currently performed with specimens obtained by amniocentesis. There are two major disadvantages of this technology: First, amniocentesis can only be performed after the 14th week of pregnancy. Second, in some instances, the risk associated with an inherited disorder is comparable to the risk associated with the surgical procedure of amniocentesis. Urine DNA based technology can present the information while avoiding both problems.

An important factor contributing to the success of any new diagnostic test is the necessity that patients and doctors express a preference for the new test. Invasive prenatal testing is often declined by the patient because of the attendant risks to the fetus and mother. If the same information can be obtained from a safe and simple urine test, it is likely that the test will be given widespread acceptance by the public and medical community.

B. Analyzing for the Presence of Specific Host Nucleic Acid Sequences that Cross the Kidney Barrier The present invention further provides methods enabling the detection of specific nucleic acid sequences originating from the patient's own endogenous nucleic acid that must cross the kidney barrier to appear in the urine. The method generally involves the steps of obtaining a urine sample from a patient and subjecting the material to a method of detecting a target nucleic acid sequence. In one embodiment, the method further encompasses substantially purifying nucleic acids present in the urine sample prior to detecting the target nucleic acid. This method has a variety of diagnostic applications, including, but not limited to, tumor diagnosis and the diagnosis of diseases caused by clonal expansion of cells containing DNA modifications accompanied by death of at least a subset of the cells bearing DNA modifications.

Success of tumor treatment is currently dependent on tumor type and method of treatment. However, the most important factor determining the success of cancer therapy is detection of the tumor at the earliest possible stage of development. The earlier a tumor is detected the better is the prognosis. In many per-neoplastic conditions, such as inherited predisposition to a specific tumor type or a disease promoting neoplastic transformation, (e.g. chronic hepatitis and cirrhosis), significant efforts for early tumor detection are currently being applied but existing techniques are usually invasive and expensive. The oncologist's arsenal now includes tests that are not only invasive, often hazardous, but also less reliable than expected.

From the patient's point of view, the invasive tests are expensive and sufficiently unpleasant to warrant decisions to forgo needed tests such as rectocolonoscopy for diagnostics of colorectal cancer. The problem of compliance is of critical importance when high-risk patients are encouraged to submit to procedures that are clearly uncomfortable and unpleasant. Dramatic improvement of high-risk patient compliance is an absolute necessity for the future. Thus, development of new methods for early tumor detection is absolutely necessary for a substantial progress in this area of medicine. It is also clear that such methods should be based not only on more sensitive techniques for detection of clinical symptoms of neoplastic growth, but rather on revealing tumor cell-specific markers.

The earliest cellular changes that can be used as a marker of neoplastic transformation are changes that cause the transformation, i.e. genetic and epigenetic DNA modification. Various changes in DNA sequences and/or in the methylation status of CpG islands (especially of those located in promoter regions of tumor suppressor genes) are currently used as tumor markers. As more such markers are discovered, it has become evident that some are characteristic of early tumor stages, or even of pre-neoplastic conditions. Other DNA modifications can indicate relatively late phases of neoplastic transformation. Also there are expectations that some changes in DNA sequences and its methylation pattern will help predict metastatic potential and tumor cell sensitivity to different chemotherapeutic agents. Cell death occurs at all stages of tumor growth and detection of tumor-specific changes in the urine DNA can be an excellent marker for tumor diagnosis and monitoring of anti-tumor therapy. The example section below shows that tumor-specific mutations of the K-ras gene can be detected in the urine of patients with colorectal tumors that bear this mutation.

One of the greatest clinical challenges for tumor chemotherapy is the variable sensitivity of different tumors to anti-tumor drugs, and the absence of a simple test for the quick early stage evaluation of anti-tumor therapy. Normally, the oncologist can observe the results of treatment only after several months. Meanwhile, the tumor can continue to grow and possibly metastasize if the chemotherapeutic regimen is ineffective. One embodiment of the present invention, useful for the immediate monitoring of the effectiveness of tumor therapy, is the quantitative analysis of tumor-specific mutations in the patient's urine DNA. If the treatment is effective, then more tumor cells die, and the ratio of the mutant sequence to any normal reference sequence contained in the urine will increase. Eventually, if chemotherapy is effective the mutant tumor-specific sequence will disappear. Periodic analysis of a patient's urine DNA can be used for monitoring of possible tumor re-growth. Early indication of chemotherapeutic ineffectiveness would allow time to try other chemotherapeutics and anti-tumor treatments. This approach is similarly effective for the evaluation of the effectiveness of radiation therapy and other cancer therapies and for monitoring after surgical treatment of cancerous growths.

C. Analyzing for the Presence of Specific Non-host Nucleic Acid Sequences that Cross the Kidney Barrier The present invention also provides methods enabling the detection of specific nucleic acid sequences that do not originate from the patient's endogenous nucleic acid sequences, and must cross the kidney barrier to appear in the urine. The steps are the same as for the detection of host originated nucleic acids, except that the detection method selects for non-host nucleic acid sequences. This method has a variety of diagnostic applications, including, but not limited to, diagnosis of infection by nucleic acid containing pathogens that infect areas other than the urinary tract, and do not shed nucleic acids directly into the urinary tract.

In one embodiment, the present invention has important applications in organ and tissue transplanting science. Transplantation of different organs, tissues, and cells or other material that contains nucleic acids (referred to as "transplanted material") is now widely used in clinical practice. The most important problem faced by the transplant patient and the healthcare delivery system is the requirement to carefully control the normal immune response of the recipient that leads to transplant rejection and failure. In spite of intensive therapy designed to suppress the recipient's immune response, rejection episodes often occur during the post-transplantation period and their early detection can be very useful, if not critical for effective clinical management.

Each person has a distinct and unique pattern of genes that are encoded by DNA. Since the donor's DNA is genetically different from the recipient's DNA, the present invention can be used to "monitor transplanted material" which is defined as detecting and/or measuring the rejection or acceptance of transplanted organs, tissues and cells by the recipient. This will reduce and even eliminate in some instances the necessity of taking tissue biopsies from already debilitated patients. Example 3, below, describes a test for the appearance of Y chromosome-specific DNA sequences in the urine of female recipients who had received blood transfusions with blood from males. These experiments showed that due to the death of white blood cells from the male donor, Y chromosome-specific sequences appeared in the urine of the female recipient. These blood cells die in such the same manner as the cells of a transplanted organ that has been attacked by the recipient's immune system. Methods of the present invention can be used to track the progress of recipients of cell, tissue and organ transplants.

D. Analyzing the Form and Degree of Methylation of the Target DNA

Changes in DNA methylation of specific genomic areas affect chromatin structure and DNA transcription, and consequently, are being investigated for their involvement in various pathological processes. Analysis of transrenal DNA methylation would be a useful diagnostic tool.

Mutations and changes in DNA methylation status that happen during tumor progression can be used as the tumor markers. Esteller M, et al., Detection of Aberrant Promoter Hypermethylation of Tumor Suppressor Genes in Serum DNA from Non-Small Cell Lung Cancer Patients, Cancer Res 1999; 59:67-70. Wong IH, et al., Detection of aberrant p 16 methylation in the plasma and serum of liver cancer patients, Cancer Res 1999; 59: 71-3. Various changes in DNA sequences and/or in the methylation status (Baylin SB, et al., Alterations in DNA methylation: A fundamental aspect of neoplasia, Adv Canc Res 1998; 72:141-96) of CpG islands (especially of those located in promoter regions of tumor suppressor genes) are currently used as tumor markers. Also there are expectations that some changes in DNA sequences and its methylation pattern will help to predict metastatic potential and tumor cell sensitivity to different chemotherapeutic agents. methylation in CpG islands of some genes, e.g. MYF-3 gene, can be bound to different stages of carcinogenesis. Hypermethylation of this gene in comparison with normla mucosa was observed in 88% of adenomas and 99% of carcinomas. Shannon B, et.al., Hypermethylation of the MYF-3 gene in colorectal cancers: associations with pathological features and with microsatellite instability, Int J Cancer 1999; 84:109-13.

There are no reliable markers based on DNA mutations for HCC. However, in this case there is a growing group of markers that are based on CpG island methylation in a gene promoter region, e.g. the p16 or GSTPI promoter. p16 methylation was found in more than 70% of HCC tissues and among HCC cases with aberrant methylation similar changes were also detected in about 80% of the plasma samples. Wong IH, et al., Detection of aberrant p16 methylation in the plasma and serum of liver cancer patients, Cancer Res 1999; 59:71-3. Matsuda Y, et al., p16(INK4) is inactivated by extensive CpG methylation in human heptocellular carcinoma, Gastroenterology 1999; 116:394-400. Somatic hypermethylation of GSTP1 CpG islands was observed in DNA from more than 80% of HCC cases. Tchou JC, et al., GSTP1 CpG island DNA hypermethylation in hepatocellular carcinomas, Int J Oncol 2000; 16:663-76.

We have already discussed how methylation of CpG islands in promoters of tumor suppressor genes leading to their inactivation, is involved in pre-neoplastic conditions and carcinogenesis, and can be used for diagnostics of those pathological processes. Methylation of estrogen-receptor gene has been linked to heart disease (Fricker J. Heart disease linked to oestrogen-receptor gene methylation. Mol. Med. Today, 5, 505-506, 1999). Fragile X chromosome syndrome is associated not only with the expansion of the number of CGG trinucleotide tandem repeats at the 5' untranslated region of the FMR1 gene but also with hypermethylation in the CGG repeats and the adjacent CpG islands (Panagopoulos I, et al., A methylation PCR approach for detection of fragile X syndrome. Hum. Mutat., 14, 71-79, 1999). Analysis of the methylation status at the CpG islands of the small nuclear ribonucleoprotein associated polypeptide N (SNRPN) gene using amniotic fluid cell cultures or cultivated chorionic vilus samples has been recommended for prenatal diagnosis of Prader-Willi and Angelman syndromes (Kubota T, et al., Analysis of parent of origin specific DNA methylation at SNRPN and PW71 in tissues: implication for prenatal diagnosis. J. Med. Genet., 33, 1011-1014, 1996). DNA hypermethylation of the promoter region of the E-cadherin gene is characteristic of chronic hepatitis and liver cirrhosis (Kanai Y, et al., Aberrant DNA methylation precedes loss of heterozygosity on chromosome 16 in chronic hepatitis and liver cirrhosis. Cancer Lett., 148, 73-80, 2000). Of course many more modifications in DNA methylation status will be linked to various disease in the future. Detection of those modifications in transrenal DNA will be a useful marker in prenatal testing as well as for diagnosis of pathological processes in adult organisms.

It is known that aging is accompanied by specific changes in the genome methylation status, hypermethylation of some CpG islands and demethylation in coding regions of genome (Toyota M and Issa J-PJ. CpG islands methylator phenotypes in aging and cancer. Seminars in Cancer Biol., 9, 349-357, 1998). Detection of these changes in transrenal DNA, that contains DNA fragments from various cell types, can be used as a marker of normal and pathological aging processes.

II. METHODS FOR NUCLEIC ACID MANIPULATION AND DETECTION

Techniques for nucleic acid manipulation useful for the practice of the present invention are described in a variety of references, including but not limited to, Molecular Cloning: A Laboratory Manual, 2nd ed., Vol. 1-3, eds. Sambrook et al. Cold Spring Harbor Laboratory Press (1989); and Current Protocols in Molecular Biology, eds. Ausubel et al., Greene Publishing and Wiley-Interscience: New York (1987) and periodic updates. Specific descriptions, while not intended to limit the scope of the present invention, provide guidance in practicing certain aspects of the present invention.

A. Reducing Degradation by DNase

DNA is subject to degradation by DNases present in urine. The present invention encompasses several methods for preventing or reducing the degradation of DNA while in urine so that sufficiently large sequences are available for detection by known methods of DNA detection such as those described below. In one embodiment, samples of urine are taken when the urine has been held in the bladder for less than 12 hours, in a specific embodiment the urine is held in the bladder for less than 5 hours, more preferable for less than 2 hours. Collecting and analyzing a urine sample before it has been held in the bladder for a long period of time reduces the exposure of DNA to the any DNase present in the urine.

In another embodiment of the present invention, after collection, the urine sample is treated using one or more methods of inhibiting DNase activity. Methods of inhibiting DNase activity include, but are not limited to, the use of ethylenediaminetetraacetic acid (EDTA), guanidine-HCl, GITC (Guanidine isothiocyanate), N-lauroylsarcosine, Na-dodecylsulphate (SDS), high salt concentration and heat inactivation of DNase.

In yet another embodiment, after collection, the urine sample is treated with an adsorbent that traps DNA, after which the adsorbent is removed from the sample, rinsed and treated to release the trapped DNA for detection and analysis. This method not only isolates DNA from the urine sample, but, when used with some adsorbents, including, but not limited to Hybond N membranes (Amersham Pharmacia Biotech Ltd., Piscataway, N.J.) protects the DNA from degradation by DNase activity.

B. Increasing Sensitivity to Detection

In some cases, the amount of DNA in a urine sample is limited. Therefor, for certain applications, the present invention encompasses embodiments wherein sensitivity of detection is increased by any method(s) known in the art, including, without limitation, one or more of the following methods.

Where DNA is present in minute amounts in the urine, larger urine samples can be collected and thereafter concentrated by any means that does not effect the detection of DNA present in the sample. Some examples include, without limiting the breadth of the invention, reducing liquid present in the sample by butanol concentration or concentration using Sephadex G-25 (Pharmacia Biotech, Inc., Piscataway N.J.).

Nested PCR can be used to improve sensitivity by several orders of magnitude. Because of the vulnerability of nested PCR to inaccurate results due to DNA contamination, in one embodiment of the present invention, precautions are taken to avoid DNA contamination of the sample. For example, without limiting the present invention, one can treat PCR reagents with restriction endonuclease(s) that cleave within the target sequence, prior to adding them to the test DNA sample.

C. Substantially Purifying Nucleic Acids Prior to Detection

In one embodiment, the present invention encompasses substantially purifying or isolating nucleic acids from a sample prior to detection. Nucleic acid molecules can be isolated from urine using any of a number of procedures, which are well-known in the art. Any method for isolation that facilitates the detection of target nucleic acid is acceptable. For example, DNA can be isolated by precipitation, as described by Ishizawa et al., Nucleic Acids Res. 19, 5972 (1991). Where a large volume sample contains a low concentration of DNA, as with urine, a preferred method of isolating DNA is encompassed. In this method, a sample is treated with an adsorbent that acts to concentrate the DNA. For example, a sample can be treated with a solid material that will adsorb DNA, such as, without limitation, DEAE Sephadex A-25 (Pharmacia Biotech, Inc., Piscataway N.J.), a DNA filter, and/or glass milk. Sample DNA is eluted from the adsorbent after other compositions are washed away.

In consideration of the sensitivity of various nucleic acid analyzing techniques, such as PCR, the present invention also encompasses methods of reducing the presence of contaminating nucleic acids in the urine sample. Contamination of urine samples by nucleic acid sequences that have not crossed the kidney barrier can be introduced by cells shedding from the urinary tract lining, by sexual intercourse, or during processing of the urine sample prior to detection of the DNA sequence of interest. Without intending to limit the present invention to any mechanism, it is believed that DNA passing the kidney barrier and appearing in urine is likely to have on average a shorter length than DNA introduced from contaminating sources because of the fragmentation that occurs in apoptotic cells and necrotic cells in the body, combined with the action of DNase in the blood and urine.

Filtration can be used to reduce the level of contaminating DNA in a urine sample prior to detection, by selecting for shorter sequences of DNA. In one embodiment of the present invention nucleic acids containing more than about 1000 base pairs, or 1000 nucleotides when denatured, are removed from the sample prior to detection. In a specific embodiment of the present invention, urine samples are filtered prior to amplification by PCR to remove substantially all DNA comprising greater than 300 base pairs, or 300 nucleotides when denatured. Without limiting the invention to a specific mechanism, it is proposed that such a filtration removes contaminating DNA from cells shed from the urethral/bladder wall or introduced into the urethra during sexual intercourse. The majority of DNA from such contaminating sources are likely to comprise more than 300 nucleotides as the DNA is not for the most part a product of fragmentation of nucleic acids as a result of apoptotic cell death.

Nucleic acid molecules can also be isolated by gel electrophoresis, whereby fragments of nucleic acid are separated according to molecular weight. The technique of restriction fragments length polymorphisms (RFLP), applies the methods of electrophoresis separation, followed by nucleic acid detection enabling comparison by molecular weight of fragments from two or more alleles of a specific gene sequence.

The above-mentioned methods of purification are meant to describe, but not limit, the methods suitable for use in the invention. The methods of isolating nucleic acids are within the ability of one skilled in the art and are not described in detail here.

D. Analysis and Detection of Specific Nucleic Acid Sequences

The expression "assaying for the presence of a nucleic acid sequence" refers to the use of any method to determine whether or not a nucleic acid sequence is present in a sample. Methods include, but are not limited to, techniques for hybridization, amplification and detection of nucleic acids. One skilled in the art has access to a multitude of these methods, including, but not limited to, those set forth in Current Protocols in Molecular Biology, eds. Ausubel et al., Greene Publishing and Wiley-Interscience: New York (1987) and periodic updates. It is contemplated that two or more methods can be used in combination to confirm the results or improve the sensitivity of the assay. An example of analyzing by the combination of methods to determine whether or not a nucleic acid sequence is present is the technique of restriction fragment length polymorphism based PCR ("PCR-RFLP"), where nucleic acid sequences are amplified, treated with restriction enzymes, and separated by electrophoresis, allowing for the detection of nucleic acids containing small modifications, such as point mutations.

The terms "detect" and "analyze" in relation to a nucleic acid sequence, refer to the use of any method of observing, ascertaining or quantifying signals indicating the presence of the target nucleic acid sequence in a sample or the absolute or relative quantity of that target nucleic acid sequence in a sample. Methods can be combined with nucleic acid labeling methods to provide a signal by, for example: fluorescence, radioactivity, colorimetry, gravimetry, X-ray diffraction or adsorption, magnetism, enzymatic activity and the like. The signal can then be detected and/or quantified, by methods appropriate to the type of signal, to determine the presence or absence, of the specific DNA sequence of interest.

To "quantify" in relation to a nucleic acid sequence, refers to the use of any method to study the amount of a particular nucleic acid sequence, including, without limitation, methods to determine the number of copies of a nucleic acid sequence or to determine the change in quantity of copies of the nucleic acid sequence over time, or to determine the relative concentration of a sequence when compared to another sequence.

To assist in detection and analysis, specific DNA sequences can be "amplified" in a number of ways, including, but not limited to cycling probe reaction (Bekkaoui, F. et al, BioTechniques 20,240-248 (1996), polymerase chain reaction (PCR), nested PCR, PCR-SSCP (single strand conformation polymorphism), ligase chain reaction (LCR) (F. Barany Proc. Natl. Acad. Sci USA 88:189-93 (1991)), cloning, strand displacement amplification (SDA) (G. K. Terrance Walker et al., Nucleic Acids Res. 22:2670-77 (1994), and variations such as allele-specific amplification (ASA).

An alternative to amplification of a specific DNA sequence that can be used to indicate the presence of that sequence in methods of the present invention is based on hybridization of a nucleic acid cleavage structure with the specific sequence, followed by cleavage of the cleavage structure in a site-specific manner. This method is herein referred to as "cleavage product detection." This method is described in detail in U.S. Pat. Nos. 5,541,331 and 5,614,402, and PCT publication Nos. WO 94/29482 and WO 97/27214. It allows for the detection of small amounts of specific nucleic acid sequences without amplifying the DNA sequence of interest.

E. Detection, Analysis and Quantification of Methylated Regions of DNA

Without limiting the present invention to any specific methods of detection, analysis or quantification of methylated regions of DNA, the following techniques are useful for evaluating DNA methylation. Methods for the mapping and quantification of methylated regions of DNA, in general, and for analysis of transrenal DNA, in particular, may be grouped in two classes: methods allowing to assess overall methylation status of CpG islands and methods for analysis of sequence specific methylation.

Methods in the first group rely on Southern hybridization approach, based on utilization of properties of methylation sensitive restriction nucleases. Hatada I, et al., Proc Natl Acad Sci USA 1991 Nov 1, 1991 88(21):9523-7, describes a genomic scanning method for higher organisms using restriction sites as landmarks. Issa JP, et al., Nat Genet Aug. 7, 1994. (4):536-40, shows that methylation of the oestrogen receptor CpG island links ageing and neoplasia in human colon. Pogribny I. and Yi P, James SJ, Biochem Biophys Res Commun Sep. 7, 1999 262(3):624-8, describe a sensitive new method for rapid detection of abnormal methylation patterns in global DNA with and within CpG islands.

Recently designed DNA microarray based technology can also be included in this group. Huang TH, et al., Genet Mar. 8, 1999(3):459-70, describes methylation profiling of CpG islands in human breast cancer cells.

The methods in the second group are based on registration of the sequence differences between methylated and unmethylated alleles resulting from bisulfite treatment of DNA. Registration usually is carried out by PCR amplification using primers specific to methylated and unmethylated DNA. Herman JG, et al., Proc Natl Acad Sci USA Sep. 3, 1996; 93(18):9821-6, describes methylation-specific PCR: a novel PCR assay for methylation status of CpG islands. Depending on the experimental setting several approaches based on this strategy have been developed.

There are also several options for the quantification of methylated CpG islands in small amount of DNA (Xiong Z. and Laird PW, Nucleic Acids Res Jun. 15, 1997; 25(12):2532-4, describing COBRA: a sensitive and quantitative DNA methylation assay, and Olek A, et al., Nucleic Acids Res Dec. 15, 1996; 24(24):5064-6, describing a modified and improved method for bisulphite based cytosine methylation analysis) and partially degraded DNA received from micro-dissected pathology sections (Gonzalgo ML and Jones PA, Nucleic Acids Res Jun. 15, 1997; 25(12):2529-31, describing rapid quantitation of methylation differences at specific sites using methylation-sensitive single nucleotide primer extension (Ms-SNuPE)). Additionally, there is a methylation sensitive SSCP that was developed for the analysis multiple methylation sites in CpG islands (Kinoshita H, et al., Anal Biochem Feb. 15, 2000; 278(2):165-9, describing methods for screening hypermethylated regions by methylation-sensitive single-strand conformational polymorphism) and an extremely sensitive methylation specific Real Time PCR (Eads CA, et al., Nucleic Acids Res Apr. 15, 2000; 28(8):E32, describing MethyLight: a high-throughput assay to measure DNA methylation).

F. Detection, Analysis and Quantification of Some Other Nucleic Acid Modifications Ligation-mediated polymerase chain reaction (LMPCR) has been used for the detection of DNA adducts at individual nucleotide positions in mammalian genes. Adduct-specific enzymes, such as T4 endonuclease V, base excision repair enzymes, like UvrABC nuclease, and chemical cleavage can be used to convert the adducts into DNA strand breaks. The positions of these breaks are then detected by LMPCR. Yoon JH, and Lee CS, Mol Cells Feb. 29, 2000; 10(1):71-5, describes the mapping of altromycin B-DNA adduct at nucleotide resolution in the human genomic DNA by ligation-mediated PCR. Pfeifer, GP, et al., Proc Natl Acad Sci USA Feb. 15, 1991; 88(4):1374-8, describes the in vivo mapping of a DNA adduct at nucleotide resolution: detection of pyrimidine (6-4) pyrimidone photoproducts by ligation-mediated polymerase chain reaction. Pfeifer GP, Denissenko MF, and Tang MS, Toxicol Lett Dec. 28, 1998; 102-130:447-51, describes PCR-based approaches to adduct analysis.

Using this approach the distribution of benzo[a]pyrene diol epoxide adducts (formed by cigarette smoke major carcinogen benzo[a]pyrene) in the P53 gene was mapped at nucleotide resolution. Adduct formation was observed at the nucleotide positions that appeared to be mutational hotspots in human lung cancers. Denissenko MF, et al., Science Oct. 18, 1996; 274(5286):430-2, describes preferential formation of benzo[a]pyrene adducts at lung cancer mutational hotspots in P53. A similar trend was observed in the case of skin cancer. Tommasi S, Denissenko MF, and Pfeifer GP, Cancer Res Nov 1, 1997; 57(21):4727-30, shows that sunlight induces pyrimidine dimers occur preferentially at 5-methylcytosine bases. Thus, the distribution of DNA adducts in the p53 gene caused by environmental carcinogens corresponds to the mutational hotspots of certain cancers.

These data indicate that both quantitation of DNA adducts and their gene specific nucleotide mapping in transrenal DNA can be used for the evaluation of genotoxic effects of environmental factors, dietary and other carcinogens as well as for prediction of resulting predisposition to a specific type of cancer.

The following examples are provided to illustrate but not limit the invention

EXAMPLE 1

DETECTION OF POLYMERIC DNA IN URINE OF MICE PREINOCULATED WITH λ PHAGE DNA

This example analyzes the ability of DNA to cross the kidney barrier in rodents and appear in detectable form in urine.

λ phage DNA (New England BioLabs, MA) was labeled by nick translation with [α-$^{32}$P] dNTP DNA (New England BioLabs, MA) using the Klenow fragment of E. Coli DNA polymerase to a specific radioactivity of $10^8$ cpm/μg as previously described. (/]Sambrook J., Fritsch E. F., Maniatis T., Molecular Cloning. A Laboratory Manual. 2d Edition. Cold Spring Harbor Laboratory Press, 1989). Two months old male Wistar rats were injected subcutaneously with 0.4 μg of the [$^{32}$p] labeled DNA. Urine samples were then collected for three days and total and acid-insoluble radioactivity was measured in a liquid scintillation counter. The kinetics of excretion of acid-insoluble radioactivity in urine appear in Table 1, below. It was determined that 3.2% of the total DNA with which the rats were inoculated crossed the kidney barrier and was detected in urine and 0.06% of the total DNA appeared in the urine in an acid-insoluble form; representing polymeric nucleotides.

TABLE 1

KINETICS OF URINE EXCRETION OF INJECTED [$^{32}$P]DNA

| | 1st day | 2nd day | 3rd day | TOTAL |
|---|---|---|---|---|
| TOTAL RADIOACTIVITY | | | | |
| (CPM) | 1,080,800 | 100,800 | 7,700 | 1,189,300 |
| (% INJECTED DNA) | (2.9%) | (0.3%) | (0.02%) | (3.2%) |
| ACID-INSOLUBLE | | | | |
| RADIOACTIVITY (CPM) | 21,000 | ND | ND | 21,000 |
| (% INJECTED DNA) | (0.06%) | | | (0.06%) |

DNA from the urine samples was isolated by phenol deproteinization (Sambrook J., Fritsch E. F., Maniatis T. Molecular Cloning. A Laboratory Manual, 2d Edition. Cold Spring Harbor Laboratory Press, 1989) and subjected to electrophoresis in a 1.5% agarose gel. Gels were stained with ethidium bromide (0.5 μg/ml) for visualization of DNA. (Sambrook J., Fritsch E. F., Maniatis T. Molecular Cloning. A Laboratory Manual, 2d Edition. Cold Spring Harbor Laboratory Press, 1989).

Figure 1B:
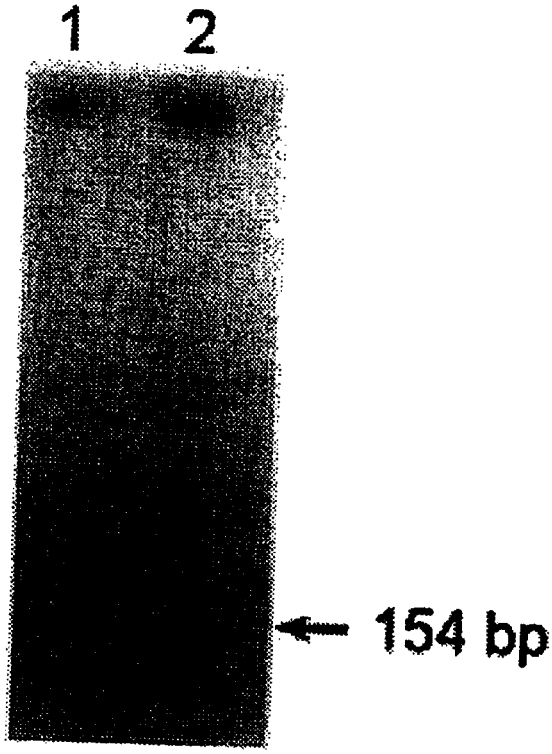
FIG. 1B is an autoradiograph of an agarose gel which depicts the detection of 32P-labeled λ phage DNA in the urine from mice injected with phage DNA. The results of two experiments (lanes 1 and 2) are presented.

FIGS. 1A and 1B depict the results of duplicate experiments (represented by lanes 1 and 2). FIG. 1A is the gel viewed by ethidium bromide staining, and FIG. 1B represents the same gel viewed by autoradiography. Labeled fragments of DNA appeared in the autoradiography representing sequences averaging approximately 150 base pairs.

The results of this experiment support that DNA can both cross the kidney barrier in polymeric form and remain in polymeric form in urine, notwithstanding the presence of DNases, for a period of time sufficient to allow a urine sample to be taken and DNA to be isolated from the urine sample. The kinetics of excretion of the injected DNA suggest that much of the injected DNA is reutilized in the body prior to appearing in the urine. It is possible that recycled radiolabeled nucleotides could later be incorporated into cells from the urinary tract and then appear in the urine without crossing the kidney barrier. However, it is unlikely that the DNA detected in this experiment could have been introduced into the urine from cells of the urinary tract, due to the short period of time between injection of labeled DNA and urine collection. While the injected DNA may eventually appear in cells of the bladder, it is unlikely to represent the same nucleic acid sequence because it is expected that the action of nucleases in the body will after a sufficient period of time cell free in the body, eventually break down the DNA to nucleotides.

EXAMPLE 2

DETECTION OF HUMAN DNA SEQUENCES IN URINE OF MOUSE PREINOCULATED WITH HUMAN CELLS

Example 1 showed that DNA sequences could remain in polymeric form in the blood stream, cross the kidney barrier, and remain suitable for subsequent detection. The next set of experiments were performed to determine if DNA from cells dying in the organism but not in the urinary tract can be detected in urine.

Human Raji lymphoma cells growing in RPMI supplemented with 5% fetal calf serum were irradiated with 1000 rads of $^{137}$CS γ-rays. Mice were then inoculated subcutaneously with $10^8$ cells each. Urine samples were collected for three days, and DNA was isolated as described above. Human-specific DNA sequences were detected by multilocus screening using Alu oligonucleotide-directed PCR as previously described, (Zietkiewicz, E., Labuda M., Sinnett D., Glorieux F. H., and Labuda D., Proc. Natl. Acad. Sci. USA, 89, 8448-8451, 1992) followed by electrophoresis in a 1.5% agarose gel.

Figure 2:
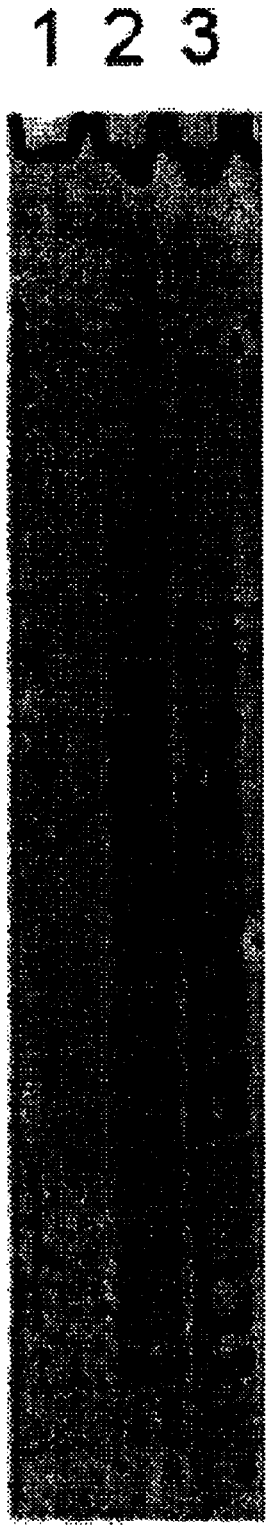
FIG. 2 is a photograph of an agarose gel which depicts the detection by gel electrophoresis of human Raji lymphoma cell DNA sequences from the urine of mice preinoculated with irradiated human cells. Lanes: 1—urine DNA from control mouse; 2—control human DNA; 3—urine DNA from mouse that was injected with human cells.

The results appear in FIG. 2. PCR amplification of urine DNA from the control animal (lane 1) did not produce any DNA fragments; and the fragments obtained from PCR amplification of the urine DNA taken from the test mouse that was injected with human cells (lane 3) did contain detectable human DNA sequences, as evidenced by a comparison with the identical bands that appear in the reference human DNA sample (lane 2).

The results support that a portion of DNA from cells dying in a mammal crosses the kidney barrier and remains in polymeric form in urine, notwithstanding the presence of DNases, for a period of time sufficient to allow a urine sample to be taken and DNA to be isolated from the urine sample. Further, one can test for the presence of specific DNA sequences in urine samples using methods such as PCR amplification of specific desired sequences that would not be present in the urine sample but for having crossed the kidney barrier in amplifiable form.

EXAMPLE 3

DETECTION OF TRANSRENAL NUCLEIC ACIDS

Taken together, Examples 1 and 2 demonstrate that, in the mouse model, both free DNA and DNA from dying cells cross the kidney barrier and can be detected in urine by PCR analysis. Two systems were selected as models to demonstrate that DNA can cross the kidney barrier and remain in polymeric form in human urine samples. The systems are designed to focus on DNA originating from cells dying outside the urinary tract rather than DNA that appears in urine due to the death of cells in the urinary tract.

Women who were either pregnant or transfused with male blood were studied because both of these models represented humans having DNA in their bodies that is not present in their normal genome. Each woman studied was analyzed for the presence of Y chromosome-specific sequences in their urine.

Detection of repeated and Single Copy Y Chromosome Specific Sequences in the Urine of Women Pregnant with Male Fetuses.

As discussed above, apoptotic cell death plays a significant role in embryogenesis. If fetal DNA crosses the placental barrier, it will appear in the mother's blood and, subsequently, in her urine. Fetal reticulocytes and white blood cells are other potential sources of fetal DNA and are also detected in the mother's blood in the first 4-5 weeks of pregnancy. Lo, Y-M. D., et al., Lancet 335:1463-1464, (1990). Bianchi, D. W., et al., Proc. Natl. Acad Sci. USA 87:3279-3283, (1990). Bianchi, D. W., et al., Proc. Natl. Acad. Sci. USA 93:705-708, (1996).

Urine samples were obtained from pregnant women at gestational ages of between 16 and 36 weeks. Fetal sex was confirmed by ultrasound screening. In previous studies, described in Example 4, below, it was found that human urine contains components that can degrade DNA (DNase). This DNase activity varies from sample to sample. To reduce DNA degradation, the following steps were taken to collect and preserve the urine samples. Urine samples (20 ml each) were collected in 50 ml Corning tubes filled with 5 ml of 250 mM ethylenediaminetetraacetic acid (EDTA) solution as a prophylactic against DNase activity. Tubes containing the urine samples were then kept at −80° C. until use.

Two methods were used for DNA isolation from the urine samples, both of which gave essentially the same results. In the first method, previously described by Ishizawa et al. (Ishizawa M., et al., Nucleic Acids Res. 19, 5972, 1991), urine samples (150 μl) were thawed at 60° C. and added to 3 volumes of a solution containing 6 M guanidine isothyocyanate (GITC), 13 mM EDTA, 0.5% sodium N-lauroylsarcosine, 10 μg glycogen, and 26 mM Tris-HCl, pH 8. The mixture was incubated at 60° C. for 15 min. in a heating block and DNA was precipitated by addition of an equal volume of isopropanol. After vigorous shaking tightly capped tubes were kept for 15 min. at room temperature and DNA was collected by centrifugation at 10,000×g for 5 minutes. The resultant pellet was washed with 80% ethanol, air-dried, dissolved in 50 μl of deionized water and treated with Chelex 100-based DNA extraction reagent (Perkin Elmer) as described (Walsh P. S., Metzger D. A., Higuchi R. BioTechniques 10, 506-513, 1991).

The present invention encompasses an alternative method of DNA isolation that is suitable for the isolation of DNA from larger samples. In this method, based on DNA adsorption on glass powder, 2.5 ml urine samples were added to an equal volume of 10 M guanidine-HCl, and the mixture was applied to a column with 0.1 ml of 5% Wizard resin (Wizard Minipreps DNA purification system, Promega). The columns were washed with a solution containing 100 mM NaCl in a 50% ethanol solution and the DNA was eluted with 100 μl of deionized water.

DNA samples purified from urine were heat denatured for 5 minutes at 95° C. followed by filtration through a Microcon 100 filter (Amicon, MA) as recommended by the supplier to separate from the sample substantially all DNA greater than 300 nucleotides in length.

Next, the samples were subjected to PCR. Each experiment had internal positive and negative controls as well as a blank sample (saline solution which was processed in the same way as the urine samples) designed to detect PCR contamination.

To reduce the chance of carryover DNA contamination of the PCR reaction mixture, the reagents were decontaminated prior to addition of a DNA sample by incubation with a restriction endonuclease specific for the target sequence: HinfI - for the Y chromosome-specific 97 base pair sequence and HaeIII for the 154 base pair sequence. The reagents were treated for 1 hour at 37° C. with 1 unit per 25 μl of reaction mixture. PCR samples were then placed into a thermocycler cell, heated at 94° C. for 3 min. to inactivate the enzyme and DNA samples were added.

Two different markers were used to detect Y chromosome-specific sequences. DYZ1 is a repeated (2000-5000 times per genome) sequence described by Nakahori Y., et al., Nucl. Acids Res. 14, 7569-7580, 1986. The single-copy gene marker DYS14 was also used to examine the ability of the methods of the present invention to detect modifications in single copy genes, such as occurs in certain genetic disorders and cancers. (Arnemann J., et al., Nucl. Acids Res. 15, 8713-8724, 1987). The single-copy sequence was analyzed using nested PCR, a more sensitive and specific PCR technique. (Lo Y-M. D., et al., Lancet 335, 1463-1464, 1990).

The following primers were used to amplify DYZ1 fragments:

(Y 1) 5'-TCCACTTTATTCCAGGCCTGTCC (SEQ ID NO: 1)

(Y2) 5'-TTGAATGGAATGGGAACGAATGG (SEQ ID NO: 2)

(YZ1) 5'-CCATTCCTTTGCATTCCGTTTCC (SEQ ID NO: 3)

(YZ2) 5'-ATCGACTGGCAGGGAACCAAAAG (SEQ ID NO: 4)

To detect DYS14 we performed nested PCR using the following primers:

(Y1.5) 5'-CTAGACCGCAGAGGCGCCAT (SEQ ID NO: 5)

(Y1.6) 5'-TAGTACCCACGCCTGCTCCGG (SEQ ID NO: 6)

(Y1.7) 5'-CATCCAGAGCGTCCCTGGCTT (SEQ ID NO: 7)

(Y1.8) 5'-CTTTCCACAGCCACATTTGTC (SEQ ID NO: 8)

Y1 and Y2 result in a 154 base pair product. Ivinson A. J., Taylor G.R. In PCR. A practical approach. (McPherson M. J., Quirke P., and Taylor G. R., eds.). IRL Press. Oxford, New York, Tokyo, pp. 15-27, 1993.

Shorter segments of DNA are believed to be more prevalent in the urine samples than are longer segments due to filtration by the kidney barrier and the action of DNase. The present invention encompasses the novel primers YZ1 and YZ2, that generate a shorter (97 base pairs) fragment, in order to maximize the power of the detection method.

To detect DYS14 we used nested PCR with the following primers: Y1.5 and Y1.6 producing a 239 base pair external fragment; and Y1.7 and Y1.8 producing a 198 base pair internal fragment. (Lo Y-M. D., et al., Lancet 335, 1463-1464, 1990).

Thirty five or forty cycles of PCR reaction were performed. Cycle conditions were as follows: denaturation at 94° C. for 30 seconds; annealing at 58° C.-63° C. (depending on primers, as described below) for 60 seconds; chain elongation at 72° C. for 30 seconds. The denaturation step was extended to 2 minutes at the beginning of the first cycle and the last chain elongation step was extended to 7 minutes. Annealing was at 63° C. for the YZ1/YZ2 primers and 58° C. for the Y1/Y2 primers. For nested PCR forty cycles with the Y1.5/Y1.6 primers were followed by 25 cycles with the Y1.7/Y1.8 primers, both at 58° C.

PCR products were analyzed in a 10% polyacrylamide gel (29: 1), 1×TBE electrophoresis buffer, 10 V/cm, for 2.5 hours, at room temperature and visualized by ethidium bromide staining.

Figure 4A:
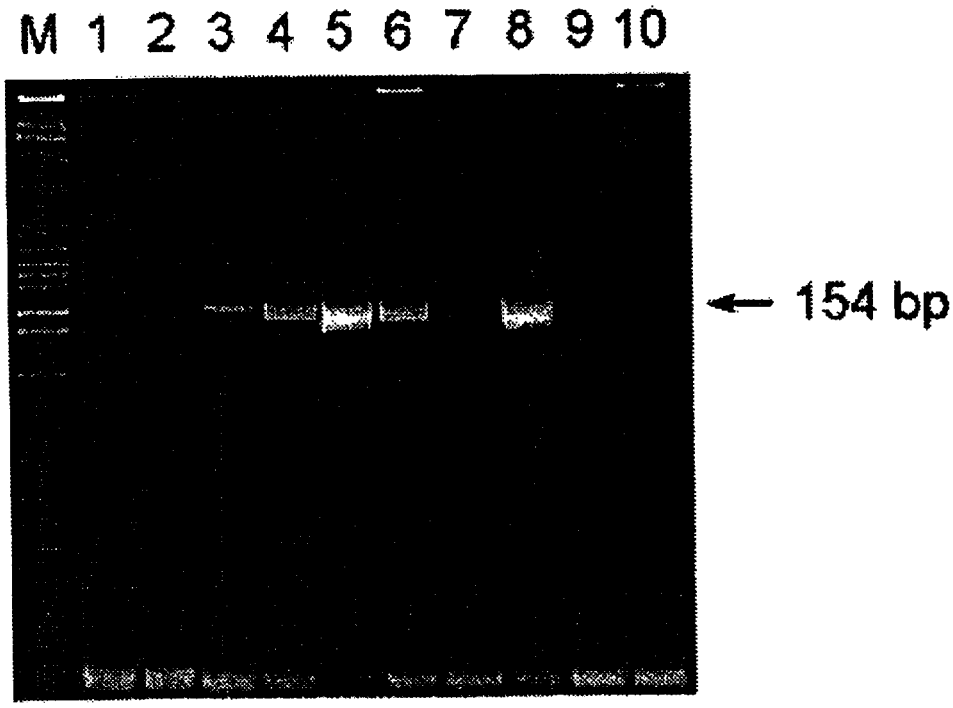
FIG. 4A is a photograph of an agarose gel which depicts the detection, in the urine of pregnant women carrying male fetuses, of a 154 base pair fragment of the Y chromosome-specific repeated DNA sequence. Lanes: M-molecular weight standard; 1—negative control (no DNA added); 2-5—positive controls (0.1, 1.0, 10 and 100 pg of total male DNA, respectively); 6 and 8—male fetuses; 7—female fetus; 9—blank sample; 10—urine DNA from non-pregnant woman.
Figure 4B:
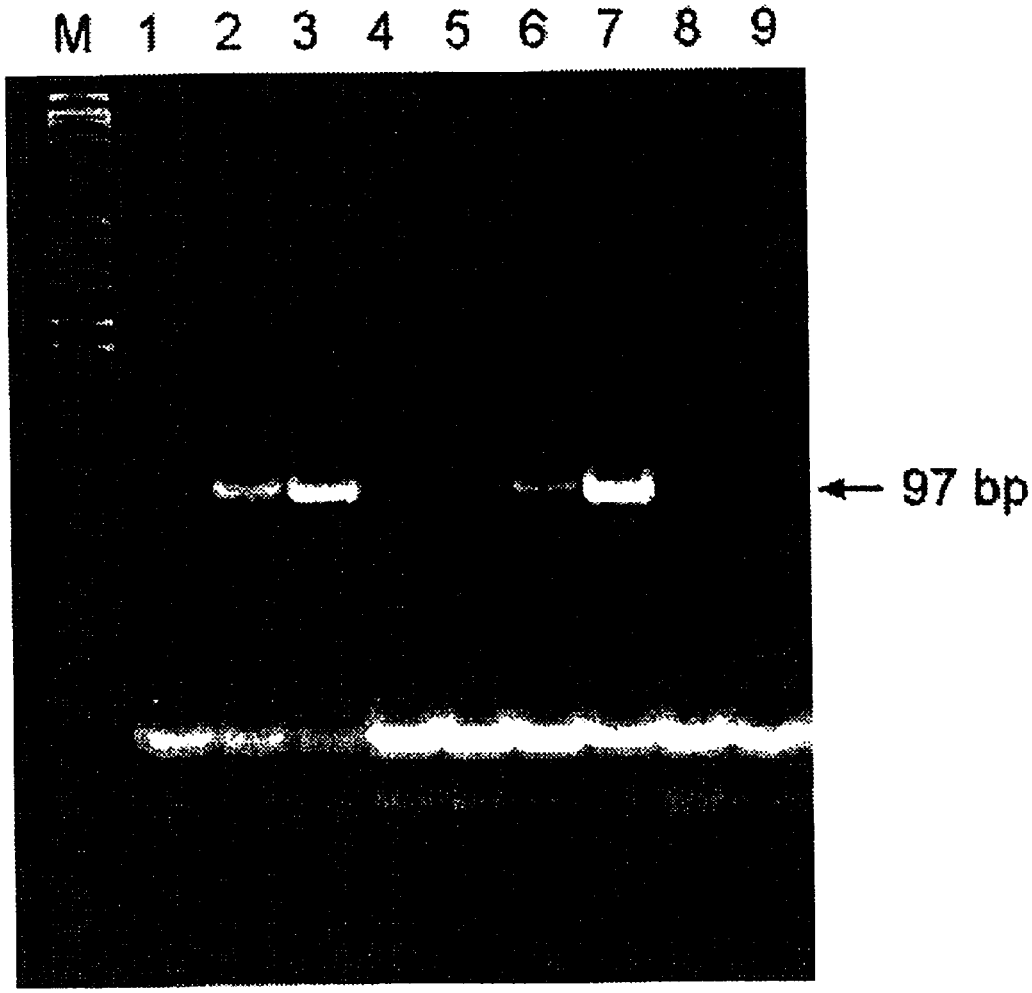
FIG. 4B is a photograph of an agarose gel which depicts the detection, in the urine of pregnant women carrying male fetuses, of a 97 base pair fragment of the Y chromosome-specific repeated DNA sequence. Lanes: M-molecular weight standard; 1-3—positive controls (0.1, 1.0 and 10 pg of male total DNA, respectively); 4 and 5—female fetuses; 6 and 7—male fetuses; 8—blank sample; 9—urine DNA from non-pregnant woman.
Figure 5:
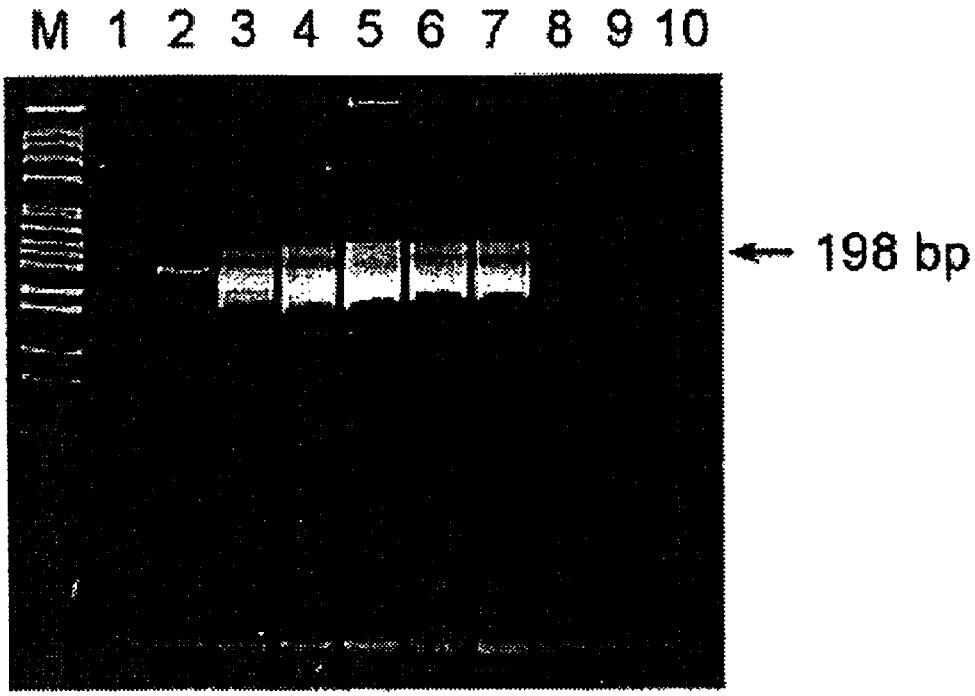
FIG. 5 is a photograph of an agarose gel which depicts the detection of a Y chromosome-specific single-copy DNA sequence (198 base pairs) in the urine of pregnant women carrying male fetuses. Lanes: M-molecular weight standard; 1—negative control (no DNA added); 2-5—positive controls (1, 10, 100 and 1000 pg of total male DNA, respectively); 6 and 7—male fetuses; 8—female fetus; 9—blank sample; 10—urine DNA from non-pregnant woman.

The results appear in FIGS. 4A, 4B and 5. In FIG. 4A, a 154 base pair PCR product of DYZ1, a repeated sequence of the Y chromosome, was detected with Y1 and Y2 primers. Lane M is an msp1 digest of pBR322 as a molecular weight standard; The negative control (lane 1, no DNA added) showed no detectable bands; the positive controls (lanes 2-5, representing 0. 1, 1.0, 10 and 100 pg of male total DNA, respectively) display bands of increasing intensity; the first group of test samples, from women carrying male fetuses (lanes 6 and 8), display clear bands of the same size as those in the positive controls; the second test sample, from a woman carrying a female fetus (Lane 7) displays no bands; two more control lanes (9 representing a blank sample and 10 representing DNA from the urine of a non-pregnant woman) show no evidence of bands.

In FIG. 4B, a 97 base pair PCR product of DYZ1 was detected with YZ-1 and YZ-2 primers. Lane M is an msp1 digest of pBR322 as a molecular weight standard; the positive controls (lanes 1-3, representing 0.1, 1.0, and 10 pg of male total DNA, respectively) display bands of increasing intensity; the first test samples, from women carrying female fetuses (lanes 4 and 5) displayed no bands; the second group of test samples, from women carrying male fetuses (lanes 6 and 7); display bands of the same size as those in the positive controls; two more control lanes (8 representing a blank sample and 9 representing DNA from the urine of a non-pregnant woman) show no evidence of bands.

In FIG. 5, a Y chromosome-specific single-copy DNA sequence (198 base pairs) was detected in the urine of pregnant women carrying male fetuses. Lane M is an msp1 digest of pBR322 as a molecular weight standard; The negative control (lane 1, no DNA added) showed no detectable bands; the positive controls (lanes 2-5, representing 0, 1, 1.0, 10 and 100 pg of male total DNA, respectively) display bands of increasing intensity; the first group of test samples, from women carrying male fetuses (lanes 6 and 7), display clear bands of the same size as those in the positive controls; the second test sample, from a woman carrying a female fetus (Lane 8) displays no bands; two more control lanes (9 representing a blank sample and 10 representing DNA from the urine of a non-pregnant woman) show no evidence of bands.

The results of these experiments support the following conclusions regarding the present invention: a fraction of DNA from cells dying in the animal or human body crosses the kidney barrier and can be detected in urine in polymeric form, notwithstanding the presence of DNases; a fraction of DNA from cells dying in the developing embryo crosses both the placental and kidney barriers and can be detected in mother's urine; the size of the cell-free urine DNA is sufficient to be amplified in PCR; and the concentration of fetal DNA in mother's urine, even in the first few months of pregnancy, is high enough to detect genes which exist only in single copy form in the fetal genome.

The results further support that maternal urine can be used as an indicator of fetal sex in specific and the composition of the fetal genome in general, where it differs from the maternal genome, which can be used for diagnosis of existing or potential disease. Analysis of fetal DNA in a pregnant mother's urine can be used for detection of sequences of DNA inherited from the male parent, including those sequences indicative of or causing disease. Thus, the results support that methods of the present invention encompass the determination of fetal sex as well as the diagnosis of certain fetal conditions which are characterized by the presence of specific DNA sequences in the fetal genome.

Detection of Y Chromosome Specific Sequences in the Urine of a Woman who has been Transfused with Male Blood.

In the case of a female transfused with a male donor's blood, the donor's dead or dying white blood cells were expected to be the source of sequences of DNA specific to the male genome in the cell-free DNA of the recipient's blood and urine.

A urine sample was obtained from a woman 10 days following a transfusion with 250 ml whole blood from a male donor. DNA from the urine was isolated and tested for the presence of a male-specific 154 base pair sequence from the Y chromosome, using Y1 and Y2 primers, by using the methods described above.

Figure 3:
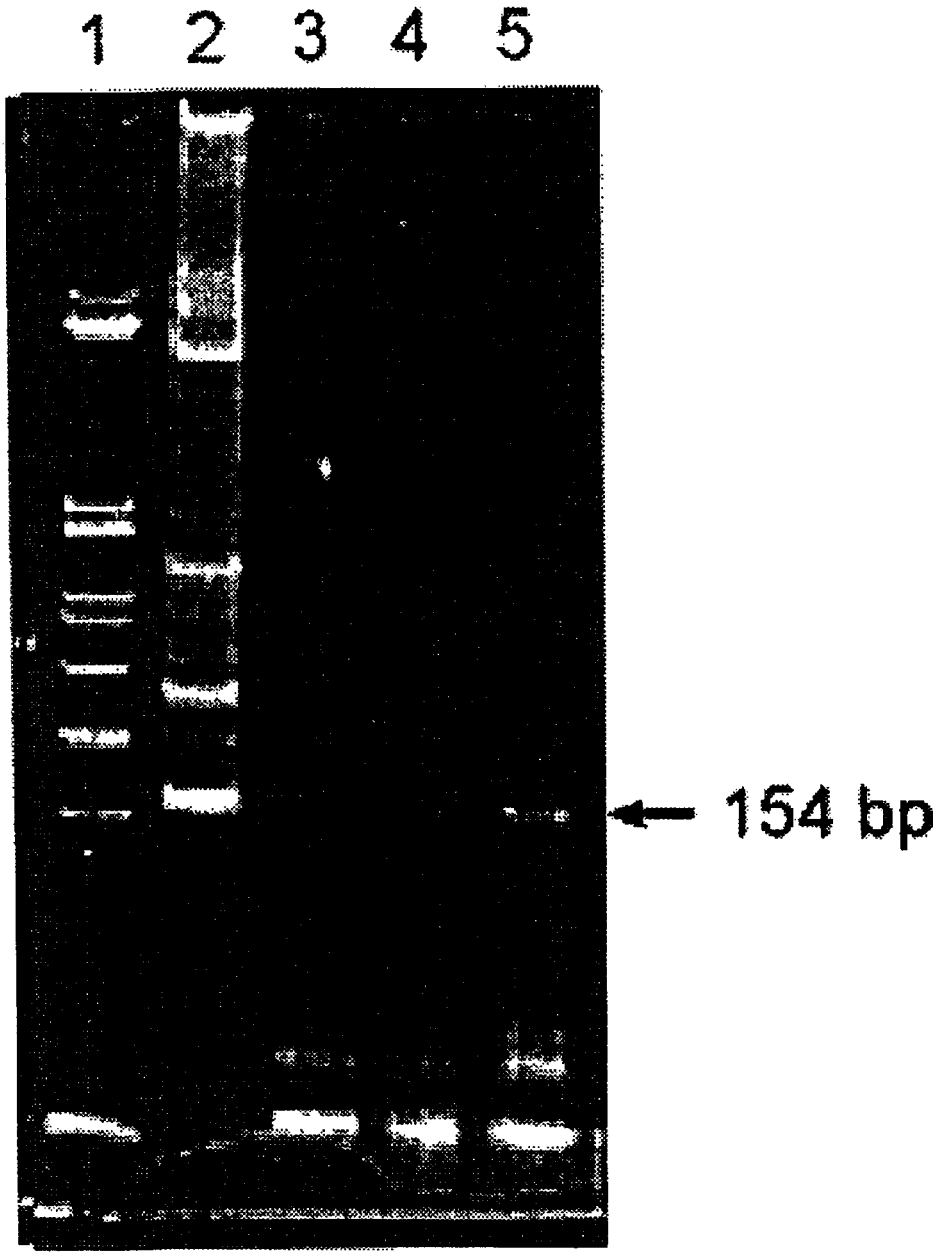
FIG. 3 is a photograph of an agarose gel which depicts the detection of Y chromosome specific sequences of DNA from the urine of a woman who had been transfused with blood from a male 10 days earlier. Lanes: 1—markers (pBR322 DNA-MspI digest); 2—positive control (0.1 μg of total DNA from lymphocytes of a male donor); 3—blank sample (salt solution passed through all the procedures of DNA isolation and analysis); 4—negative control (no added DNA); 5—urine DNA after blood transfusion.

The results appear in FIG. 3. Lane 1 is an Msp1 digest of pBR322 as a molecular weight standard; Lane 2 is a positive control (0.1 μg of total DNA from lymphocytes of a male donor) displaying a 154 base pair band of DNA; Lane 3 is a blank sample (saline solution passed through all the procedures of DNA isolation and analysis); Lane 4 is a negative control (contains no added DNA); and Lane 5, displaying a 154 base pair sequence specific to the Y chromosome, is DNA from the woman's urine sample following blood transfusion. In a subsequent study, of nine women transfused with male donor blood, a male specific band was detected in five samples. (Data not shown). Thus, in an embodiment of the present invention, various methods discussed herein, as well as any methods known in the art, can be used to improve the sensitivity of the method.

The results obtained show that, in a human, polymeric DNA released from dying blood cells can remain in polymeric form in circulating blood, cross the kidney barrier and be detected in urine by PCR. The results further show that DNA sequences released from cells with genotypes different from patients normal genotype can be selectively detected in the patient's urine. These results clearly support the application of the present invention for the diagnosis of pathologies related to genetic modifications.

EXAMPLE 4

DNASE ACTIVITY IN URINE

This example examines the activity of DNase present in urine by evaluating the kinetics of degradation of λ phage DNA in a urine sample.

Exogeneous λ phage DNA (200 pg) was added to 2.5 ml aliquots of a urine sample from a pregnant woman. Aliquots were incubated at 37° C. for various periods of time (from 0 to 2 hours), DNA was isolated and amplified by PCR (with annealing at 58° C.), as described in Example 3, to detect the presence of a λ phage DNA sequence of 200 base pairs. The following primers were used to amplify a phage lambda DNA fragment from 20722 to 20921 nucleotides:

5' CAACGAGAAAGGGGATAGTGC (SEQ ID NO: 9)

5' AAGCGGTGTTCGCAATCTGG (SEQ ID NO: 10).

Figure 6:
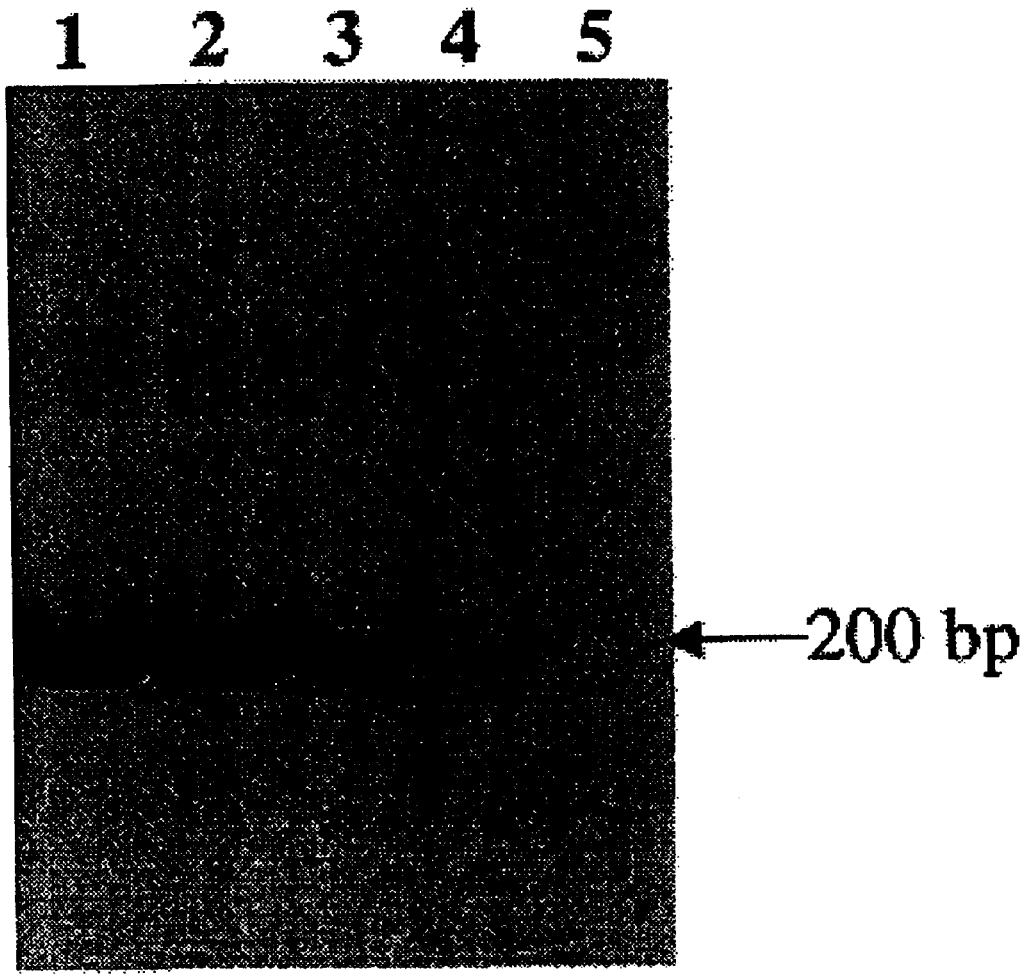
FIG. 6 is a photograph of an agarose gel which depicts the kinetics of DNA degradation over time as a result of endogenous DNase activity in urine, wherein the lanes contain the following: Lane 1—positive control (200 pg of λ phage DNA added to PCR tube); Lanes 2-5—samples incubated for 0, 30 min., 60 min. and 120 min., respectively.

The results appear in FIG. 6. Lane 1, the positive control (200 pg of λ phage DNA added to PCR tube) displays a clear band at approximately 200 base pairs; Lanes 2-5, representing samples incubated for 0, 30 min., 60 min. and 120 min., respectively, display sequentially decreasing signals. The degradation activity of DNase present in the urine is apparent from this figure. In one embodiment, the present invention encompasses the use of various methods known to one skilled in the art to prevent the degradation of DNA by DNase or other constituents of urine.

EXAMPLE 5

Urine DNA Concentration and Purification

Various methods were tested for concentrating and purifying urine samples to improve the sensitivity and accuracy of urine DNA detection.

Butenol Concentration, Nick-translated [$^{32}$P]labeled DNA, intact or denatured, was added to 20-ml samples of urine and subjected to several steps of butanol concentration. After each concentration step, the sample volume and radioactivity of 50 μL aliquots were measured. Results showed a greater than 90% reduction in sample volume over 5 extractions, with an increase of radiation of approximately 100% in the 50 μL aliquot.

Sephadex Purification. Measured amounts of dry Sephadex G-25 Coarse (Pharmacia Biotech, Inc., Piscataway N.J.), (between 2 and 4 grams, inclusive) were added to 10-ml urine samples supplemented with Dextran Blue (A630 -0.1) of 200,000 Daltons. After approximately 30 minutes swelling, the void volume was removed from the mixture by filtration under pressure and measured. The concentration value was determined by measurement of Dextran Blue absorbance at 630 nm. As the amount of Sephadex increased, the void volume fell to less than 2 ml and the concentration value increased approximately 4.5 times its original value.

Isolation Of Native And Denatured DNA By Glassmilk Adsorption. Glassmilk adsorption was also tested. Native or denatured nick-translated [32P]labeled DNA was added to 2 ml urine samples and subjected to isolation by adsorption on glass powder in the presence of 6 M guanidine isothiocyanate (GITC). The adsorbent was subsequently washed with GITC, followed by a wash with isopropanol. Then, the DNA was recovered in TE. Between 80 and 90% of the DNA, both native and denatured, was recovered by this method. It was noted that the use of ionic detergents such as EDTA, that can be used to protect DNA from DNAse activity, can also have an adverse effect on the adsorption process of some materials, including glass beads. Thus, the samples were not treated with EDTA prior to glassmilk adsorption.

EXAMPLE 6

Detection of DNA in Urine by Hybridization

This example evaluates hybridization as a technique for DNA detection for use in methods of the present invention. Urine samples were collected from pregnant women.

DNA samples isolated from 1 ml of urine were blotted onto Zeta-Probe membrane (Bio-Rad, Calif.) in 0.4 M NaOH, 10 mM EDTA using a Bio-Dot SF microfiltration apparatus (Bio-Rad). Pre-hybridization and hybridization procedures were performed by incubation in formamide based hybridization solution at 42° C. for 16 hours as previously described (Sambrook et al., 1989). A DNA fragment of 979 base pairs (DYZ1 -p) amplified by PCR from a Y Chromosome specific repeated DYZ1 sequence was used as a probe for hybridization. Novel PCR primers designed to amplify this fragment are as follows:

L1: 5'-CCAATCCCATCCAATCCAATCTAC (SEQ ID NO: 11)

L2: 5'-GCAACGCAATAAAATGGCATGG (SEQ ID NO: 12)

DNA probes were labeled with [$\alpha$-$^{32}$P] dCTP, by random priming, to a specific radioactivity of over $5\times10^8$ counts per minute (cpm)/μg. Hybridization membranes were washed with 2×SSC, 0.1% SDS at room temperature twice, followed by two high stringency washes with 0.1×SSC, 0.1% SDS at 65° C. Kodak X-Omat AR film, with Fisher Biotech L-Plus intensifying screen, was exposed to the filters at room temperature for 2-16 hours.

The results appear in FIG. 7. The negative control (lane 1, non-pregnant female) shows no signal; the positive control (lane 2, male total genome DNA, 5 ng) displays hybridization; the urine samples from women carrying male fetuses (lanes 3,4) have marked signals; and the urine samples from women carrying female fetuses (lanes 5, 6) show significantly lower signal, easily distinguished from the positive test and control samples. The faint band in lanes 6 and 7 may be a result of contaminating DNA from the surroundings. In the figure, clear bands appear only in the positive control and the urine from pregnant women carrying male fetuses. Thus, hybridization is an effective technique for detection of DNA in urine for methods of the present invention, such as the detection of specific nucleic acid sequences that have crossed the kidney barrier, and more specifically, the determination of fetal sex. While hybridization technique indicates a clear distinction between samples which are positive and negative for the presence of the target sequence of DNA, the methods of the present invention also encompass the application of techniques to control the introduction of contaminating DNA into the samples prior to hybridization or amplification.

EXAMPLE 7

Early Prenatal Sex Detection

This example investigates the feasibility of detecting fetal DNA in maternal urine at early gestational ages. It is known that fetal cells appear in maternal blood at gestational ages as early as 5-9 weeks (Eggling et al., "Determination of the origin of single nucleated cells in maternal circulation by means of random PCR and a set of length polymorphisms," (1997) Hum. Genet. 99, 266-270; Thomas et al., "The time of appearance, and quantitation, of fetal DNA in the maternal circulation," (1994) Annals NY Ac. Sci 731, 217-225). One can suggest that apoptosis is especially active at early stages of embryonic development and, hence, an enhanced input of degraded DNA into maternal circulation can be expected at that time, making such early detection possible.

To this end, pregnant women attending an antenatal clinic to have deliberate abortion (gestation ages of 5-12 weeks) were investigated with informed consent. Fresh urine samples taken just prior to operation as well as samples of embryonic tissues removed during surgery were collected.

Urine DNA was prepared for PCR amplification by two methods-simple urine dilution or adsorption onto anion exchanger DEAE-Sephadex A-25 (Parmacia Biotech, Inc. Piscataway, N.J.). The simple urine dilution samples were 10-fold diluted with distilled water, heated in a boiling bath and used for PCR (5-10 μl per tube, i.e., 0.5-1 μl of original urine). DEAE-Sephadex A-25 purification was performed as follows. A small volume of urine (1-1.5 ml) was passed through a DEAE-Sephadex A-column (10-ml volume) to remove impurities and salts. The eluate samples obtained were taken directly to PCR. The concentration of urine DNA obtained by adsorption on anion exchanger DEAE-Sephadex A-25 appeared to be significantly higher (approximately 500-700 ng/ml) than that estimated previously (2-20 ng/ml). DNA concentration was determined by spectrofluorometry with Hoechst 33258.

PCR was performed as set forth in Example 3, above, with the following primers. Fetal sex was determined by PCR analysis of DNA from fetal tissue with Y1 (SEQ ID NO:1) and Y2 (SEQ ID NO:2) primers to amplify a 154 base pair Y-specific DYZ1 sequence. Because the amount of fetal DNA was sufficient, it was not necessary to perform nested PCR. Nested PCR was carried out with maternal urine DNA samples additionally using nY1 and nY2 primers to target a 77 base pair sequence found within the 154 base pair sequence:

nY1: 5'-GTCCATTACACTACATTCCC-3' (SEQ ID NO:13)

nY2: 5'-AATGCAAGCGAAAGGAAAGG-3' (SEQ ID NO:14).

The results appear in FIG. 8. In 2 out of 5 male fetuses, Y-specific sequences were detected in maternal urine DNA at gestational ages of 7-8 weeks.

EXAMPLE 8

Prenatal Testing for Congenital Diseases The principal finding of permeability of the kidney barrier for substantial sized DNA molecules opens the way for the use of maternal urine to perform completely noninvasive prenatal diagnosis of congenital diseases. One can perform such a noninvasive screen as follows.

First, a sample of urine is gathered from a pregnant woman. Where desired, polymeric DNA in the urine sample can then be isolated, purified and/or treated to prevent degradation using methods known in the art, including, but not limited to, the methods described herein. Polymeric DNA that has crossed the kidney barrier is then amplified using primers specific to known disease associated genetic anomalies, or is otherwise treated to produce a detectable signal if the specific anomaly is present. Finally, the product of DNA amplification, or the signal produced, is analyzed to determine whether or not a disease associated anomaly is present in the urine DNA. Where such an anomaly is detected and the mother does not carry the anomaly in her genome, it can be deduced that the fetus carries the anomaly.

EXAMPLE 9

Filter Transfer of DNA

As shown in the above examples, nested PCR permits detection of small amounts of DNA in urine. Thus, it was desired to determine whether DNA could be analyzed directly from the urine, rather than having to perform a DNA isolation step prior to amplification or other detection methods.

Female urine samples were collected (approximately 20 ml each) and treated with several concentrations of male DNA. 3.5 cm. Hybond N filters (Amersham) were pretreated with 0.25 N HCl for 1.5 hours to remove any contaminating DNA, followed by rinsing with distilled water. Two filters were immersed in each urine sample and allowed to incubate overnight at room temperature with gentle shaking. The filters were then removed and rinsed with distilled water.

Figure 9:
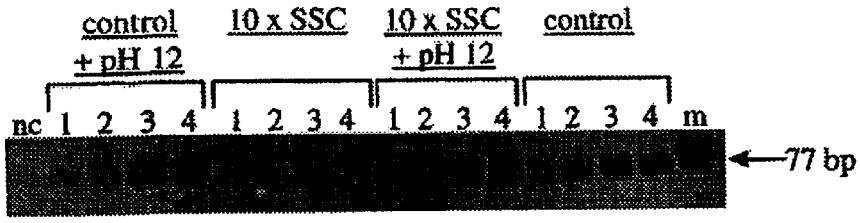
FIG. 9 is a photograph of an agarose gel showing the effect on PCR of the adsorption of urine DNA on Hybond N filters under various conditions. Lanes 1-4-20 fg, 1 pg, 2 pg or 10 pg male DNA were added per 1 μof female urine. Control - 10 μl aliquots of 10-fold diluted urine were taken directly into PCR tubes. Other urine samples were made highly concentrated in salt (10×SSC) or alkaline (adjusted to pH 12 with NaOH) and handled with "filter transfer" method nc- negative control; m-molecular weight standard.

DNA was desorbed by incubation of the filters with 450 μl 0.25×PCR buffer in a boiling bath for 10 minutes. An aliquot (5-10 μl, i.e. 0.5-1.0 μl of original urine sample) was taken from each sample for nested PCR. The results appear in FIGS. 9 and 10. In FIG. 9, lanes 1-4 represent 20 fg, 1 pg, 2 pg, and 10 pg male DNA, respectively, per 1 μl of female urine. The Control contained 10 μl aliquots of 10-fold diluted urine, taken directly into PCR tubes. Other urine samples were made highly concentrated in salt (10×SSC) or alkaline (adjusted to pH 12 with NaOH) and handled with the "filter transfer" method described herein. nc—negative control; m—molecular weight standard. It is clear from the figure that the simple filter transfer method provides a stronger signal than can be detected from a transfer of an equivalent amount of urine.

Figure 10A:
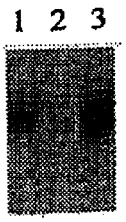
FIGS. 10A, 10B, and 10C are photographs of an agarose gel showing the effect of the adsorption of urine DNA using Hybond N filters on DNA degradation. A-control (lanes: 1-10 μl aliquot of 10-fold diluted urine was taken directly into PCR tubes just after male DNA addition; 2-10 μl aliquot of 10-fold diluted urine was taken directly into PCR tubes after incubation overnight at room temperature; 3-Hybond N filter was incubated in urine overnight and used for DNA filter transfer (10 μl aliquot of eluate from filter was used for the analysis). B—all the procedures as in A, except the urine samples were made 10 mM in EDTA. C—all the procedures as in A, except the urine samples were made 10 mM in EDTA and adjusted to pH 12.
Figure 10B:
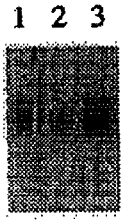
Figure 10C:
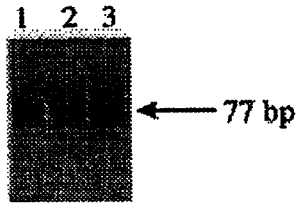

Additionally, as FIG. 10 shows, adsorption of urine DNA on Hybond N filters appears to have protected the DNA from nuclease digestion. This protection was complimented by increasing the pH of the sample. Section A represents the controls (lanes: 1-10 μl aliquot of 10-fold diluted urine was taken directly into PCR tubes just after male DNA addition; 2-10 μl aliquot of 10-fold diluted urine was taken directly into PCR tubes after incubation overnight at room temperature; 3—Hybond N filter was incubated in urine overnight and used for DNA crossover (10 μl aliquot from eluate was used for the analysis). Section B—all the procedures as in A, except the urine samples were made 10 mM in EDTA. Section C—all the procedures as in A, except the urine samples were made 10 mM in EDTA and adjusted to pH 12.

EXAMPLE 10

Tumor Diagnostics

The ability to isolate significant quantities of DNA from urine samples, as shown in Example 3, also introduces the ability to evaluate a patient, in a non-invasive fashion, for the presence of one or more of numerous DNA anomalies that indicate the existence of or the propensity for a disease of interest. Such a method has applications for the early diagnosis and treatment of many cancers and pathogen infections that are not characterized by shedding of cells directly into the urinary tract, such as, but not limited to, cancers or infections that exist in isolated areas of the body and are not easily detectable by other means. One can perform such a noninvasive screen as follows.

First, a sample of urine is gathered from a patient. Where desired, polymeric DNA in the urine sample can then be isolated, purified and/or treated to prevent degradation using methods known in the art, including, but not limited to, the methods described herein. Polymeric DNA that has crossed the kidney barrier is then amplified using primers specific to known disease associated genetic anomalies, or is otherwise treated to produce a detectable signal if the specific anomaly is present.

Some methods of amplification result in improved specificity when applied to detect small changes in DNA, such as point mutations. For example, highly sensitive PCR double RFLP method (PCR-dRFLP) (Grau and Griffais, NAR, 1994, 22, 5773-5774) can be used to diagnose a mutation that creates or destroys a natural or artificial restriction site. However, PCR-RFLP sometimes presents a technical difficulty because a defective restriction enzyme activity can be confused with the loss of the restriction site. Moreover, the presence of a restriction site can be experimentally easier to ascertain than its absence. To overcome this difficulty, two modified nested PCR amplifications can additionally be performed for each studied DNA, one pair of PCR primers being designed to introduce a restriction site specific for the wild-type allele while the second pair of primers being designed to introduce a restriction site specific for the mutant allele. Each PCR product is then analyzed by RFLP. These two RFLP allow a less ambiguous interpretation of the results. Essentially, it as though each mutation abolishes a restriction site on the wild type sequence to create a new one on the mutant one.

Finally, the product of DNA amplification, or the signal produced, is analyzed to determine whether or not a disease associated anomaly is present in the urine DNA, thereby permitting non-invasive diagnosis of many diseases characterized by modification of a patient's DNA.

EXAMPLE 11

Further Tumor Diagnostics

In this example, K-ras mutations were detected in the urine of patients with colon adenocarcinomas and pancreatic carcinomas.

Samples of colon cancer and surrounding "normal" tissues were obtained from patients undergoing surgery. Urine samples were obtained 24 hr before surgery.

Samples (25-50 ml) were collected fresh (i.e., accumulated during morning hours). The first voiding of the day was not used. The samples were adjusted to 10 mM EDTA and stored frozen before use. To control a potential contamination of solutions and final probes with exogeneous DNA the experimental setup also included a control (25 ml of saline solution) that was carried through all subsequent procedures.

DNA was purified form non-fractionated urine samples (i.e., not subjected to centrifugation) to avoid possible DNA losses due to adsorption to particulate material. Urine samples (3-5 ml) were mixed 1:1.5 (v:v) with 6 M guanidine isothiocyanate and DNA was adsorbed on a Wizard column (Minipreps DNA purification system, Promega), as recommended by the manufacturer. Columns were washed with 50% isopropanol and DNA was eluted with 200 μl of distilled water.

K-ras mutations were detected by a two-stage PCR assay using selective restriction enzyme digestions of an artificially created site to enrich for mutant K-ras DNA. Kopreski MS, et al., Detection of mutant K-ras DNA in plasma or serum of patients with colorectal cancer, Br. J. Cancer 1997; 76:1293-99. PCR was performed with oligonucleotide primers K-ras-L (5'-ACTGAATATAAACTTGTGGTAGTTGGACCT-3') (SEQ ID NO: 15) and K-ras-R (5'-TCAAAGAATGGTCCTGGACC-3') (SEQ ID NO: 16). The first primer, which is immediately upstream of codon 12, is modified at nucleotide 28 (G to C) to create an artificial restriction enzyme site (Bst NI). The oligonucleotide K-ras-R is also modified at the base 17 (C to G) to create an artificial Bst NI site to serve as an internal control for completion of the digestion. As a result, non-restricted PCR product is 157 base pairs (bp) long, while being restricted at both sites (wild type sequence) becomes 113 bp long and restricted only at right site (the left side is modified by mutation) becomes 142 bp long. The reaction mixture is cycled 15 times at 94° C. for 48 sec., 56° C. for 90 sec., and 72° C. for 155 sec. An aliquot of 10 μl adjusted to 1×Bst NI reaction buffer was digested with 10 units of Bst NI at 60° C. for 90 min. Ten μl of the digested PCR mixture was removed to a new tube and a new reaction mixture was set up for the second amplification step (35 cycles—94° C. for 48 sec., 56° C. for 90 sec., and 72° C. for 48 sec.) using identical constituents. A second Bst NI restriction digestion was performed using 25 μl of the second-step PCR product at 60° C. for 90 min. The final digestion product was separated by electrophoresis through a 3% Nu-Sieve agarose gel or 12% polyacrylamide gel.

Fresh urine samples were centrifuged 10 min at 800×g and DNA was isolated from the supernatant as described above. DNA samples were stained with 0.1 μg/ml of Hoechst 33258 and DNA concentration was determined by spectrofluorometry as described. Labarca C. and Paigen K. A simple, rapid, and sensitive DNA assay procedure. Analyt Biochem 1980; 102: 344-52.

Two groups of patients were analyzed for K-ras mutations in their urine DNA. It is known that 80-90% of pancreatic carcinomas show K-ras mutations. The first group consisted of 8 patients with pancreatic cancer (stage IV). K-ras mutations were detected in 5 of the 8 urine samples from these patients.

The second group consisted of 7 colorectal cancer patients with advanced disease (stages III-IV). Urine samples were taken 24 hr before surgery and tissue samples, tumor and surrounding normal tissue, were obtained during surgery. Thus, three samples obtained from each patient, tumor, normal tissue and urine DNA, were analyzed. K-ras mutations were detected in 5 out of 7 tumors. In 4 of 5 patients with tumor K-ras mutations, the same mutations were also detected in the urine samples. Two patients that had no mutation in the tumor and 9 healthy volunteers did not show K-ras mutations in their urine DNA.

In conclusion, K-ras mutations were found in 5/8 urine samples obtained from patients with pancreatic cancer as well as in urine of 4/5 patients with colorectal adenocarcinomas that have corresponding mutation in their tumors. The results of this experiment support that the in one embodiment of the present invention, methods are useful for the detection and monitoring of tumor growth, including the evaluation of the effectiveness of tumor chemo- or radiotherapy.

EXAMPLE 12

ANALYSIS OF DNA METHYLATION

For the analysis of DNA methylation we will use a methylation specific PCR strategy (Herman JG, et al., Methylation-specific PCR: A novel PCR assay for methylation status of CpG islands, Proc Natl Acad Sci US 1996; 93: 9821-26) and its recent modification for Real Time PCR (Eads CA, et al., MethyLight: a high-throughput assay to measure DNA methylation, Nucl Acids Res 2000 28: 32e-40e). The method is based on registration of the sequence differences between methylated and unmethylated alleles resulting from the bisulfide treatment of DNA. The bisulfite modification includes several steps of chemical treatments resulting in the conversion of unmethylated cytosine residues into uracil while the methylated derivatives remain unchanged. Wang RY, et al., Comparison of bisulfite modification of 5-methyldeoxycytidine and deoxycytidine residues, Nucl Acids Res 1980; 8: 4777-90.

For the high resolution CpG methylation mapping we will use +ddC-sequencing reaction.

Three pairs of primers are needed for the amplification and resolution of a methylated and unmethylated CpG island. First, primers that are specific to the "wild" type (unconverted); second, methylated/converted primers, and third, unmethylated/converted primers. To increase the sensitivity of the reaction, a second set of nested PCR primers may be needed. For the real time PCR analysis an additional DNA probe, bearing reporter dye, will be used that is specific to an amplified fragment.

Although the foregoing invention has been described in some detail by way of illustration and example for purposes of clarity of understanding, it will be apparent to those skilled in the art that certain changes and modifications can be practiced. Therefore, the descriptions and examples should not be construed as limiting the scope of the invention, which is delineated by the appended claims.

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1

tccactttat tccaggcctg tcc                                              23


<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
```

-continued ttgaatggaa tgggaacgaa tgg 23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 3 ccattccttt gcattccgtt tcc 23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 4 atcgactggc agggaaccaa aag 23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 5 ctagaccgca gaggcgccat 20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 6 tagtacccac gcctgctccg g 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 7 catccagagc gtccctggct t 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 8 ctttccacag ccacatttgt c 21

-continued

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 9 caacgagaaa ggggatagtg c 21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 10 aagcggtgtt cgcaatctgg 20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 11 ccaatcccat ccaatccaat ctac 24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 12 gcaacgcaat aaaatggcat gg 22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 13 gtccattaca ctacattccc 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 14 aatgcaagcg aaaggaaagg 20

-continued

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15

actgaatata aacttgtggt agttggacct                                    30


<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16

tcaaagaatg gtcctggacc                                               20
```

We claim:

1. A method of monitoring [transplanted material] *rejection or acceptance of cells, tissue or organs that are transplanted in areas other than the urinary tract* in a patient, comprising:

a) providing [a] urine sample*s from a patient* suspected of containing *cell-free, transrenal* nucleic acid*s* [of the transplanted material, which transplanted material is located outside of the urinary tract] *from the cells, tissue or organs that are transplanted in areas other than the urinary tract in the patient*; and b) *quantitatively* analyzing said urine sample [for nucleic acids from the cell genome of the transplanted material that are different from nucleic acids of the recipient and that have crossed the kidney barrier] *for one or more specific sequences of the cell-free, transrenal nucleic acids from dying cells in the transplanted cells, tissues or organs that are different from sequences of nucleic acids of the patient wherein said analyzing comprises the step of detecting said one or more specific sequences of nucleic acids from the transplanted cells, tissues or organs in the nucleic acids that are no more than 1000 nucleotides in length from urine samples and have crossed the kidney barrier to monitor rejection or acceptance of the transplanted cells, tissues or organs*.

[2. The method of claim 1, wherein said nucleic acid sequence is not present in cells of the urinary tract of said patient.]

3. The method of claim 1, wherein said analyzing comprises amplifying [said nucleic acid sequence with a primer substantially complementary to a part of said nucleic acid sequence that does not occur in cells of the urinary tract of the patient, to make amplified target DNA, and detecting the presence of said amplified target DNA] *the one or more specific sequences of said the cell-free, transrenal nucleic acids from step (b) and detecting the presence of said amplified target nucleic acid sequences*.

4. The method of claim 3, wherein amplifying comprises performing a polymerase chain reaction.

5. The method of claim 1, further comprising [step (a)(i)] reducing [DNA] *nucleic acid* degradation in said urine sample*s*.

6. The method of claim 5, wherein reducing [DNA degradation is by treatment] *nucleic acid degradation comprises inhibiting nuclease activity by increased pH, increased salt concentration, heat inactivation, or by treating said urine samples* with a compound selected from the group consisting of:

ethylenediaminetetraacetic acid, guanidine-HCl, guanidine isothiocyanate, N-lauroylsarcosine, and [Na-] *sodium* dodecylsulphate.

7. The method of claim 1, wherein said urine sample*s* [has] *have* been held in the bladder less than 12 hours.

8. The method of claim 1, further comprising [step (a)(i)] substantially isolating said [nucleic acid sequence] *cell-free, transrenal nucleic acids*.

9. The method of claim 8, wherein said [nucleic acid sequence is] *cell-free, transrenal nucleic acids from step (b) are* substantially isolated by precipitation.

10. The method of claim 8, wherein said [nucleic acid sequence is] *cell-free, transrenal nucleic acids from step (b) are* substantially isolated by adsorption *of said nucleic acids* on a resin.

11. The method of claim 1, further comprising [step (a)(1)] filtering said urine sample*s* to remove contaminants.

12. The method of claim 11, wherein said filtering removes [DNA] *nucleic acids* comprising more than about 1000 nucleotides.

*13. The method of claim 1, wherein said cell-free, transrenal nucleic acids from step (b) are DNA.*

*14. The method of claim 1, wherein said cell-free, transrenal nucleic acids from step (b) are RNA.*

*15. The method of claim 11, wherein said filtering removes nucleic acids comprising more than about 1000 base pairs.*

*16. The method of claim 11, wherein said filtering removes nucleic acids comprising more than about 300 nucleotides.*

*17. The method of claim 13, wherein said filtering removes nucleic acids comprising more than about 300 base pairs.*

*18. A method of monitoring cells, tissues or organs transplanted in areas other than the urinary tract in a patient, comprising:*

*a) obtaining an urine sample from said patient;*

*b) reducing nucleic acid degradation in said urine sample, wherein said reducing comprises inhibiting*

*nuclease activity by increased pH, increased salt concentration, heat inactivation, or by treating said urine sample with a compound selected from the group consisting of: ethylenediaminetetraacetic acid, guanidine-HCl, guanidine isothiocyanate, N-lauroylsarcosine, and sodium dodecylsulphate;*

*c) obtaining a fraction of nucleic acids that are made up of fewer than about 300 base pairs from said urine sample and have crossed the kidney barrier; and*

*d) analyzing said fraction for one or more specific sequences of non-patient nucleic acids from the transplanted cells, tissues or organs that are different from sequences of nucleic acids of the patient and have crossed the kidney barrier to monitor the cells, tissues or organs transplanted in areas other than the urinary tract in the patient.*

*19. The method of claim 18, wherein said urine sample has been held in the bladder less than 12 hours.*

*20. The method of claim 18, further comprising substantially isolating said nucleic acids in step (c).*

*21. The method of claim 20, wherein said isolating is by adsorption of said nucleic acids on a resin.*

*22. A method of monitoring cells, tissues or organs transplanted in areas other than the urinary tract in a patient, comprising:*

*a) obtaining an urine sample from said patient;*

*b) filtering said urine sample to remove contaminants;*

*c) obtaining a fraction of nucleic acids that are made up of fewer than about 300 base pairs from said urine sample and have crossed the kidney barrier; and*

*d) analyzing said fraction for one or more specific sequences of non-patient nucleic acids from the transplanted cells, tissues or organs that are different from sequences of nucleic acids of the patient and have crossed the kidney barrier to monitor the cells, tissues or organs transplanted in areas other than the urinary tract in the patient.*

*23. A method of detecting non-host nucleic acids originating in areas other than the urinary tract in a patient, comprising:*

*a) obtaining an urine sample from said patient, wherein said urine sample has been held in the bladder less than 12 hours;*

*b) removing nucleic acids greater than 1000 nucleotides from said urine sample; and*

*c) analyzing said urine sample for one or more specific sequences of non-patient nucleic acids that are different from sequences of nucleic acids of the patient and have crossed the kidney barrier wherein said analyzing comprises the step of detecting said one or more specific sequences in the nucleic acids less than 1000 nucleotides in length from said urine sample.*

*24. A method of detecting non-host nucleic acids originating in areas other than the urinary tract in a patient, comprising:*

*a) obtaining an urine sample from said patient;*

*b) substantially isolating said non-host nucleic acids by using a solid adsorbent material or by adsorption of said non-host nucleic acids on a resin and recovering nucleic acids that are no more than 1000 nucleotides in length from said non-host nucleic acids; and*

*c) analyzing said urine sample for one or more specific sequences of said non-host nucleic acids that are different from sequences of nucleic acids of the patient and have crossed the kidney barrier wherein said analyzing comprises the step of detecting said one or more specific sequences from the non-host in the nucleic acids no more than 1000 nucleotides in length.*

*25. A method of detecting non-host nucleic acids originating in areas other than the urinary tract in a patient, comprising:*

*a) obtaining an urine sample from said patient;*

*b) filtering said urine sample to remove contaminants and obtaining non-host nucleic acids that are no more than 1000 nucleotides in length; and*

*c) analyzing said urine sample for one or more specific sequences of non-host nucleic acids that are different from sequences of nucleic acids of the patient and have crossed the kidney barrier wherein said analyzing comprises the step of detecting said one or more specific sequences from the non-host in the nucleic acids less than 1000 nucleotides in length.*

*26. The method of claim 25, wherein said filtering removes nucleic acids comprising more than about 300 nucleotides.*

*27. The method of claim 25, wherein said filtering removes nucleic acids comprising more than about 300 base pairs.*

*28. The method of claim 25, wherein said analyzing comprises quantifying said non-host nucleic acids.*

*29. A method of detecting nucleic acids of a pathogen, wherein said nucleic acids originate in areas other than the urinary tract in a patient, comprising:*

*(a) obtaining an urine sample from said patient; and*

*(b) analyzing said urine sample for one or more specific sequences of pathogen nucleic acids that are different from sequences of nucleic acids of the patient and are from pathogen nucleic acids that are no more than 1000 nucleotides in length and that have crossed the kidney barrier wherein said analyzing comprises the step of detecting said one or more specific sequences from the pathogen.*

*30. The method of claim 29 wherein said pathogen nucleic acids are DNA.*

*31. The method of claim 29 wherein said pathogen nucleic acids are RNA.*

*32. The method of claim 29 wherein the pathogen is selected from the group consisting of a virus, a bacterium, a fungus, a mycoplasma, and a protozoan.*

*33. The method of claim 32, wherein the pathogen is a virus.*

*34. The method of claim 32, wherein the pathogen is a fungus.*

*35. The method of claim 32, wherein the pathogen is a mycoplasma.*

*36. The method of claim 32, wherein the pathogen is a protozoan.*

*37. The method of claim 32, wherein the pathogen is a bacterium.*

*38. The method of claim 29, wherein said step of analyzing said urine sample includes a technique selected from the group consisting of hybridization, cycling probe reaction, polymerase chain reaction, nested polymerase chain reaction, PCR to analyze single strand conformation polymorphisms, ligase chain reaction, strand displacement amplification and PCR to analyze restriction fragments length polymorphisms.*

*39. The method of claim 29, wherein said step of analyzing said urine sample includes a polymerase chain reaction that uses primers sufficiently complementary to hybridize with a target sequence of said pathogen nucleic acids of said pathogen.*

*40. The method of claim 29, wherein nucleic acid degradation in said urine sample is reduced.*

*41. The method of claim 40, wherein reducing nucleic acid degradation comprises inhibiting nuclease activity by increased pH, increased salt concentration, heat inactivation, or by treating said urine sample with a compound selected from the group consisting of: ethylenediaminetetraacetic acid, guanidine-HCI guanidine isothiocyanate, N-lauroylsarcosine, and sodium dodecylsulphate.*

*42. The method of claim 29, wherein said urine sample has been held in the bladder less than 12 hours.*

*43. The method of claim 29, wherein step (b) comprises substantially isolating said pathogen nucleic acids in said urine sample.*

*44. The method of claim 43, wherein said isolation is by precipitation.*

*45. The method of claim 43, wherein said isolation is by using a solid adsorbent material.*

*46. The method of claim 43, wherein said isolation is by adsorption of said pathogen nucleic acids on a resin.*

*47. The method of claim 29, further comprising filtering said urine sample to remove contaminants.*

*48. The method of claim 47, wherein said filtering removes nucleic acids comprising more than about 1000 nucleotides.*

*49. The method of claim 47, wherein said filtering removes nucleic acids comprising more than about 1000 base pairs.*

*50. The method of claim 47, wherein said filtering removes nucleic acids comprising more than about 300 nucleotides.*

*51. The method of claim 47, wherein said filtering removes nucleic acids comprising more than about 300 base pairs.*

*52. The method of claim 29, wherein said analyzing comprises quantifying said pathogen nucleic acids.*

*53. A method of detecting nucleic acids of a virus, wherein said nucleic acids originate in areas other than the urinary tract in a patient, comprising:*

*(a) obtaining an urine sample from said patient,*

*(b) analyzing said urine sample for one or more specific sequences of viral nucleic acids that are different from sequences of nucleic acids of the patient and are from viral nucleic acids that are no more than 1000 nucleotides in length and that have crossed the kidney barrier wherein said analyzing comprises the step of detecting said one or more specific sequences from the virus.*

*54. The method of claim 53, wherein said viral nucleic acids are DNA.*

*55. The method of claim 53, wherein said viral nucleic acids are RNA.*

*56. The method of claim 53, wherein said step of analyzing said urine sample includes a technique selected from the group consisting of hybridization, cycling probe reaction, polymerase chain reaction, nested polymerase chain reaction, PCR to analyze single strand conformation polymorphisms, ligase chain reaction, strand displacement amplification and PCR to analyze restriction fragments length polymorphisms.*

*57. The method of claim 53, wherein said step of analyzing said urine sample includes a polymerase chain reaction that uses primers sufficiently complementary to hybridize with a target sequence of said viral nucleic acids.*

*58. The method of claim 53, wherein nucleic acid degradation in said urine sample is reduced.*

*59. The method of claim 58, wherein reducing nucleic acid degradation comprises inhibiting nuclease activity by increased pH, increased salt concentration, heat inactivation, or by treating said urine sample with a compound selected from the group consisting of: ethylenediaminetetraacetic acid, guanidine-HCI, guanidine isothiocyanate, N-lauroylsarcosine, and sodium dodecylsulphate.*

*60. The method of claim 53, wherein said urine sample has been held in the bladder less than 12 hours.*

*61. The method of claim 53, wherein step (b) comprises substantially isolating said viral nucleic acids in said urine sample.*

*62. The method of claim 61, wherein said isolation is by precipitation.*

*63. The method of claim 61, wherein said isolation is by using a solid adsorbent material.*

*64. The method of claim 61, wherein said isolation is by adsorption of said nucleic acids on a resin.*

*65. The method of claim 53, further comprising filtering said urine sample to remove contaminants.*

*66. The method of claim 65, wherein said filtering removes nucleic acids comprising more than about 1000 nucleotides.*

*67. The method of claim 65, wherein said filtering removes nucleic acids comprising more than about 1000 base pairs.*

*68. The method of claim 65, wherein said filtering removes nucleic acids comprising more than about 300 nucleotides.*

*69. The method of claim 65, wherein said filtering removes nucleic acids comprising more than about 300 base pairs.*

*70. The method of claim 53, wherein said analyzing comprises quantifying said viral nucleic acids.*

*71. A method of detecting nucleic acids of a bacterium, wherein said nucleic acids originate in areas outside the urinary tract in a patient, comprising:*

*(a) obtaining an urine sample from said patient; and*

*(b) analyzing said urine sample for one or more specific sequences of bacterial nucleic acids that are different from sequences of nucleic acids of the patient and are from bacterial nucleic acids that are no more than 1000 nucleotides in length and that have crossed the kidney barrier wherein said analyzing comprises the step of detecting said one or more specific sequences from the bacteria.*

*72. The method of claim 71, wherein said bacterial nucleic acids are DNA.*

*73. The method of claim 71, wherein said bacterial nucleic acids are RNA.*

*74. The method of claim 71, wherein said step of analyzing said urine sample includes a technique selected from the group consisting of hybridization, cycling probe reaction, polymerase chain reaction, nested polymerase chain reaction, PCR to analyze single strand conformation polymorphisms, ligase chain reaction, strand displacement amplification and PCR to analyze restriction fragments length polymorphisms.*

*75. The method of claim 71, wherein said step of analyzing said urine sample includes a polymerase chain reaction that uses primers sufficiently complementary to hybridize with a target sequence of said nucleic acids of a bacterium.*

*76. The method of claim 71, wherein nucleic acid degradation in said urine sample is reduced.*

*77. The method of claim 76, wherein reducing nucleic acid degradation comprises inhibiting nuclease activity by*

*increased pH, increased salt concentration, heat inactivation, or by treating said urine sample with a compound selected from the group consisting of: ethylenediaminetetraacetic acid, guanidine-HCl, guanidine isothiocyanate, N-lauroylsarcosine, and sodium dodecylsulphate.*

*78. The method of claim 71, wherein said urine sample has been held in the bladder less than 12 hours.*

*79. The method of claim 71, wherein step (b) comprises substantially isolating said bacterial nucleic acids in said urine sample.*

*80. The method of claim 79, wherein said isolation is by precipitation.*

*81. The method of claim 79, wherein said isolation is by using a solid adsorbent material.*

*82. The method of claim 79, wherein said isolation is by adsorption of said nucleic acids on a resin.*

*83. The method of claim 71, further comprising filtering said urine sample to remove contaminants.*

*84. The method of claim 83, wherein said filtering removes nucleic acids comprising more than about 1000 nucleotides.*

*85. The method of claim 83, wherein said filtering removes nucleic acids comprising more than about 1000 base pairs.*

*86. The method of claim 83, wherein said filtering removes nucleic acids comprising more than about 300 nucleotides.*

*87. The method of claim 83, wherein said filtering removes nucleic acids comprising more than about 300 base pairs.*

*88. The method of claim 71, wherein said analyzing comprises quantifying said bacterial nucleic acids.*

*89. A method of testing an urine sample from a patient for target non-host nucleic acids in urine, comprising:*

*(a) obtaining an urine consisting of said target non-host nucleic acids that are no more than 1000 nucleotides in length from a patient; and*

*(b) analyzing said urine sample for one or more specific sequences of said target non-host nucleic acids that are different from sequences of nucleic acids of the patient and have crossed the kidney barrier wherein said analyzing comprises the step of detecting said one or more specific sequences in said urine sample.*

*90. The method of claim 89, wherein said target nucleic acids are DNA.*

*91. The method of claim 89, wherein said target nucleic acids are RNA.*

*92. The method of claim 89, wherein said step of analyzing said urine sample includes a technique selected from the group consisting of hybridization, cycling probe reaction, polymerase chain reaction, nested polymerase chain reaction, PCR to analyze single strand conformation polymorphisms, ligase chain reaction, strand displacement amplification and PCR to analyze restriction fragments length polymorphisms.*

*93. The method of claim 89, wherein said step of analyzing said urine sample includes a polymerase chain reaction that uses primers sufficiently complementary to hybridize with the target nucleic acids.*

*94. The method of claim 89, wherein nucleic acid degradation in said urine sample is reduced.*

*95. The method of claim 94, wherein reducing nucleic acid degradation comprises inhibiting nuclease activity by increased pH, increased salt concentration, heat inactivation, or by treating said urine sample with a compound selected from the group consisting of: ethylenediaminetetraacetic acid, guanidine-HCl, guanidine isothiocyanate, N-lauroylsarcosine, and sodium dodecylsulphate.*

*96. The method of claim 89, wherein said urine sample has been held in the bladder less than 12 hours.*

*97. The method of claim 89, wherein step (b) comprises substantially isolating said target nucleic acids in said urine sample.*

*98. The method of claim 97, wherein said isolation is by precipitation.*

*99. The method of claim 97, wherein said isolation is by using a solid adsorbent material.*

*100. The method of claim 97, wherein said isolation is by adsorption of the target nucleic acids on a resin.*

*101. The method of claim 89, further comprising filtering said urine sample to remove contaminants.*

*102. The method of claim 101, wherein said filtering removes nucleic acids comprising more than about 300 nucleotides.*

*103. The method of claim 101, wherein said filtering removes nucleic acids comprising more than about 300 base pairs.*

*104. The method of claim 89, wherein said analyzing comprises quantifying said target non-host nucleic acids.*

*105. A method of detecting non-host nucleic acids originating in areas other than the urinary tract in a patient, comprising:*

*a) obtaining an urine sample from said patient;*

*b) reducing nucleic acid degradation in said urine sample, wherein said reducing nucleic acid degradation comprises inhibiting nuclease activity by increased pH, increased salt concentration, heat inactivation, or by treating said urine sample with a compound selected from the group consisting of ethylenediaminetetraacetic acid, guanidine-HCl, guanidine isothiocyanate, N-lauroylsarcosine, and sodium dodecylsulphate;*

*c) obtaining a fraction of nucleic acids that are made up of fewer than about 300 base pairs from said urine sample and have crossed the kidney barrier; and*

*d) analyzing said fraction for one or more specific sequences of non-host nucleic acids that are different from sequences of nucleic acids of the patient and have crossed the kidney barrier wherein said analyzing comprises the step of detecting said one or more specific sequences from the non-host in said fraction.*

*106. The method of claim 105, wherein said urine sample has been held in bladder less than 12 hours.*

*107. The method of claim 105, wherein said non-host nucleic acids in said urine sample are substantially isolated by precipitation.*

*108. The method of claim 105, wherein said non-host nucleic acids in said urine sample are substantially isolated using a solid adsorbent material.*

*109. The method of claim 105, wherein said non-host nucleic acids in said urine sample are substantially isolated by adsorption of said non-host nucleic acids on a resin.*

*110. The method of claim 105, further comprising filtering said urine sample to remove contaminants.*

*111. The method of claim 105, wherein said analyzing comprises quantifying said non-host nucleic acids.*

*112. A method of detecting nucleic acids of a pathogen, wherein said nucleic acids originate in areas other than the urinary tract in a patient, comprising:*

*a) obtaining an urine sample suspected of containing said nucleic acids of a pathogen from said patient;*

*b) obtaining a fraction of nucleic acids that are made up of fewer than about 300 base pairs from said urine sample; and*

*c) analyzing said fraction for one or more specific sequences of pathogen nucleic acids that are different from sequences of nucleic acids of the patient and are from pathogen nucleic acids that have crossed the kidney barrier wherein said analyzing comprises the step of detecting said one or more specific sequences from the pathogen in said fraction.*

*113. The method of claim 112, wherein the pathogen is a virus.*

*114. The method of claim 112, wherein the pathogen is a fungus.*

*115. The method of claim 112, wherein the pathogen is a protozoan.*

*116. The method of claim 112, wherein the pathogen is a bacterium.*

*117. The method of claim 112, further comprising reducing said nucleic acid degradation in said urine sample, wherein reducing said nucleic acid degradation comprises inhibiting nuclease activity by increased pH, increased salt concentration, heat inactivation, or by treating said urine sample with a compound selected from the group consisting of: ethylenediaminetetraacetic acid, guanidine-HCl, guanidine isothiocyanate, N-lauroylsarcosine, and sodium dodecylsulphate.*

*118. The method of claim 112, wherein said urine sample has been held in the bladder less than 12 hours.*

*119. The method of claim 112, wherein said nucleic acids of said pathogen in said urine sample are substantially isolated by precipitation.*

*120. The method of claim 112, wherein said nucleic acids of said pathogen in said urine sample are substantially isolated using a solid adsorbent material.*

*121. The method of claim 112, wherein said nucleic acids of said pathogen in said urine sample are substantially isolated by adsorption of said nucleic acids on a resin.*

*122. The method of claim 112, further comprising filtering said urine sample to remove contaminants.*

*123. The method of claim 112, wherein said analyzing comprises quantifying said nucleic acids.*

*124. A method of detecting nucleic acids of a virus, wherein said nucleic acids originate in areas other than the urinary tract in a patient, comprising:*

*a) obtaining an urine sample from said patient;*

*b) reducing nucleic acid degradation in said urine sample, wherein said reducing nucleic acid degradation comprises inhibiting nuclease activity by increased pH, increased salt concentration, heat inactivation, or by treating said urine sample with a compound selected from the group consisting of ethylenediaminetetraacetic acid, guanidine-HCl, guanidine isothiocyanate, N-lauroylsarcosine, and sodium dodecylsulphate;*

*c) obtaining a fraction of nucleic acids that are made up of fewer than about 300 base pairs from said urine sample; and*

*d) analyzing said fraction for one or more specific sequences of viral nucleic acids that are different from sequences of nucleic acids of the patient and are from viral nucleic acids that have crossed the kidney barrier wherein said analyzing comprises the step of detecting said one or more specific sequences from the virus in said fraction.*

*125. The method of claim 124, wherein said urine sample has been held in the bladder less than 12 hours.*

*126. The method of claim 124, wherein said nucleic acids of said virus in said urine sample are substantially isolated by precipitation.*

*127. The method of claim 124, wherein said nucleic acids of said virus in said urine sample are substantially isolated using a solid adsorbent material.*

*128. The method of claim 124, wherein said nucleic acids of said virus in said urine sample are substantially isolated by adsorption of said nucleic acids on said virus on a resin.*

*129. The method of claim 124 further comprising filtering said urine sample to remove contaminants.*

*130. The method of claim 124 wherein said analyzing comprises quantifying said viral nucleic acids.*

*131. A method of detecting nucleic acids of a bacterium, wherein said nucleic acids originate in areas outside the urinary tract in a patient, comprising:*

*a) obtaining an urine sample from said patient;*

*b) reducing nucleic acid degradation in said urine sample, wherein said reducing nucleic acid degradation comprises inhibiting nuclease activity by increased pH, increased salt concentration, heat inactivation, or by treating said urine sample with a compound selected from the group consisting of ethylenediaminetetraacetic acid, guanidine-HCl, guanidine isothiocyanate, N-lauroylsarcosine, and sodium dodecylsulphate;*

*c) obtaining a fraction of nucleic acids that are made up of fewer than about 300 base pairs from said urine sample; and*

*d) analyzing said fraction for one or more specific sequences of bacterium nucleic acids that are different from sequences of nucleic acids of the patient and are from bacterium nucleic acids that have crossed the kidney barrier wherein said analyzing comprises the step of detecting said one or more specific sequences from the bacterium in said fraction.*

*132. The method of claim 131, wherein said urine sample has been held in the bladder less than 12 hours.*

*133. The method of claim 131, wherein said nucleic acids of said bacterium in said urine sample are substantially isolated by precipitation.*

*134. The method of claim 131, wherein said nucleic acids of said bacterium in said urine sample are substantially isolated using a solid adsorbent material.*

*135. The method of claim 131, wherein said nucleic acids of said bacterium in said urine sample are substantially isolated by adsorption of said nucleic acids on a resin.*

*136. The method of claim 131, further comprising filtering said urine sample to remove contaminants.*

*137. The method of claim 131, wherein said analyzing comprises quantifying said bacterium nucleic acids.*

* * * * *